US012697025B2

(12) United States Patent　　(10) Patent No.:　US 12,697,025 B2

De Sisternes et al.　　　　　　　(45) Date of Patent:　　　Aug. 4, 2026

(54) **OCT *EN FACE* PATHOLOGY SEGMENTATION USING CHANNEL-CODED SLABS**

(71) Applicants:Carl Zeiss Meditec, Inc., Dublin, CA (US); Carl Zeiss Meditec AG, Jena (DE)

(72) Inventors:　Luis De Sisternes, San Francisco, CA (US); Niranchana Manivannan, Fremont, CA (US)

(73) Assignees: CARL ZEISS MEDITEC, INC., Dublin, CA (US); CARL ZEISS MEDITEC AG, Jena (DE)

( * ) Notice:　　Subject to any disclaimer, the term of this patent is extended or adjusted under 35 U.S.C. 154(b) by 533 days.

(21) Appl. No.:　17/914,539

(22) PCT Filed:　Apr. 28, 2021

(86) PCT No.:　　PCT/EP2021/061147

§ 371 (c)(1),
(2) Date:　　　Sep. 26, 2022

(87) PCT Pub. No.: WO2021/219727

PCT Pub. Date: Nov. 4, 2021

(65)　　　　　Prior Publication Data

US 2023/0140881 A1　　May 11, 2023

Related U.S. Application Data

(60) Provisional application No. 63/017,574, filed on Apr. 29, 2020.

(51) Int. Cl.
A61B 3/10　　　　(2006.01)
A61B 3/12　　　　(2006.01)

(52) U.S. Cl.
CPC ............ A61B 3/102 (2013.01); A61B 3/1241 (2013.01); *G06T 2207/10101* (2013.01); *G06T 2207/20084* (2013.01)

(58) Field of Classification Search
CPC .................. A61B 3/102; A61B 5/0066; A61B 2090/3735; A61B 3/12; A61B 3/1233;
(Continued)

(56)　　　　　References Cited

U.S. PATENT DOCUMENTS

2014/0218686 A1　8/2014　Reisman
2015/0201829 A1　7/2015　Yang et al.
(Continued)

FOREIGN PATENT DOCUMENTS

CN　　　107909102　　　4/2018
CN　　　109308701　　　2/2019
(Continued)

OTHER PUBLICATIONS

Japan Patent Office; Japanese Office Action filed Dec. 4, 2024 in Application No. 2022-564330.
(Continued)

*Primary Examiner* — Atiba O Fitzpatrick
(74) *Attorney, Agent, or Firm* — SNELL & WILMER L.L.P.

(57)　　　　　ABSTRACT

A system and method for use with optical coherence tomography (OCT) data to identify a target pathology extracts multiple pathology-characteristic images from the OCT data. The extracted pathology-characteristic images may include a mixture of OCT structural images (including retinal layer thickness information) and OCT angiography images. Optionally, other pathology-characteristic images and data maps (mapped to corresponding positions in the OCT data), such as fundus images and visual field test maps may be accessed as additional pathology-characteristic
(Continued)

images. Each pathology-characteristic image defines a different image channel (e.g., "color channel") per pixel in a composite, channel-coded image, which is then used to train a neural network to search for the target pathology in OCT data. The trained neural network may then receive new composite, channel-coded image and identify/segment the target pathology within the new channel-coded image.

18 Claims, 15 Drawing Sheets

(58) Field of Classification Search
CPC ........ A61B 3/1241; G06T 2207/10101; G06T 2207/30041; G06T 2207/20081; G06T 2207/20084; G06T 9/002; G06T 5/60; G06T 2207/30104; G06T 2211/404; A61F 2009/00851; A61N 5/1017; G06K 9/6256; G06K 9/6257; G06K 9/6259; G06V 10/70; G06V 10/82; G06V 10/774–7796; G06V 10/454; G06N 3/02–126; G06N 20/00–20; G06F 18/214–2155; G06F 7/023; G06F 40/16; G01N 29/4481
See application file for complete search history.

(56) References Cited

U.S. PATENT DOCUMENTS

| | | | |
|---|---|---|---|
| 2016/0284103 A1 | 9/2016 | Huang | |
| 2017/0119242 A1 | 5/2017 | Jia et al. | |
| 2019/0272631 A1* | 9/2019 | Shemonski | A61B 3/102 |
| 2020/0193592 A1* | 6/2020 | Arienzo | A61B 5/0071 |
| 2020/0342595 A1* | 10/2020 | Jia | G06T 7/0012 |
| 2021/0153738 A1* | 5/2021 | Jia | A61B 3/1233 |
| 2021/0204809 A1 | 7/2021 | Hirose et al. | |
| 2021/0279874 A1 | 9/2021 | Boyd et al. | |
| 2021/0319556 A1* | 10/2021 | Chauhan | G06T 7/0014 |
| 2021/0369195 A1* | 12/2021 | Russakoff | G06N 3/0464 |
| 2022/0151490 A1* | 5/2022 | Jia | A61B 5/7267 |
| 2022/0301152 A1* | 9/2022 | Yim | A61B 5/4842 |
| 2023/0036463 A1* | 2/2023 | Yang | G06T 7/12 |
| 2023/0045859 A1* | 2/2023 | Halperin | G16H 50/70 |
| 2024/0095876 A1* | 3/2024 | Bagherinia | G06T 3/14 |

FOREIGN PATENT DOCUMENTS

| | | |
|---|---|---|
| CN | 110010219 | 7/2019 |
| JP | 2014147780 | 8/2014 |
| JP | 2015136626 | 7/2015 |
| JP | 2014516646 | 11/2017 |
| JP | 2018515297 | 6/2018 |
| JP | 2019-177032 | 10/2019 |
| JP | 2019531817 | 11/2019 |
| WO | 2012149175 | 11/2012 |
| WO | 2019210079 | 10/2019 |
| WO | 2020066324 | 4/2020 |

OTHER PUBLICATIONS

Japan Patent Office; Japanese Final Office Action dated Jul. 29, 2025 in Application No. 2022-564330.

Lee, et al., "Fully automated plaque characterization in intravascular OCT images using hybrid convolutional and lumen morphology features", Scientific Reports, [Online] dated Feb. 2020, Retrieved from the Internet: url: https://www.nature.com/articles/s41598-020-59315-6.

Indian Patent Office, Indian Office Action dated Jan. 30, 2026 in Application No. 202217065736.

Chinese Patent Office, Chinese Office Action dated Dec. 19, 2025 in Application No. 2021800292845.

Chinese Patent Office, Chinese Search Report dated Dec. 19, 2025 in Application No. 2021800292845.

Manivannan, et al., "Automated segmentation of geographic atrophy using U-Net on custom-generated SD-OCT en face images" Investigative Opthalmology & Visual Science, [Online] vol. 60, No. 11, dated Aug. 2019, Retrieved from the Internet: url: https://iovs.arvojournals.org/article.aspx?articleid=2748249.

Niu, et al., "Fully automated prediction of geographic atrophy growth using quantitative SD-OCT imaging biomarkers" Investigative Opthalmology & Visual Science, [Online] vol. 57, No. 12, dated Sep. 2016, Retrieved from the Internet: url: https://iovs.arvojournals.org/article.aspx?articleid=2558896.

Wu, et al., "Geographic atrophy segmentation in SD-OCT images using synthesized fundus autofluorescence imaging" IComput Methods Programs Biomed, 2019, Retrieved from the Internet: url: https://pubmed.ncbi.nlm.nih.gov/31600644/.

* cited by examiner

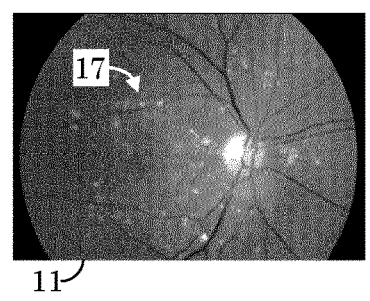 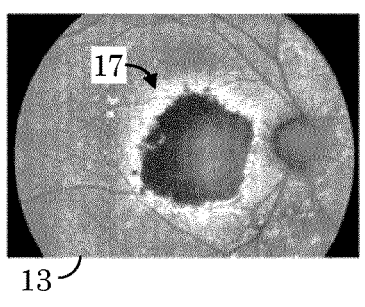 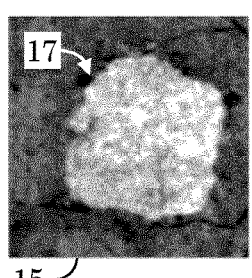
FIG. 1
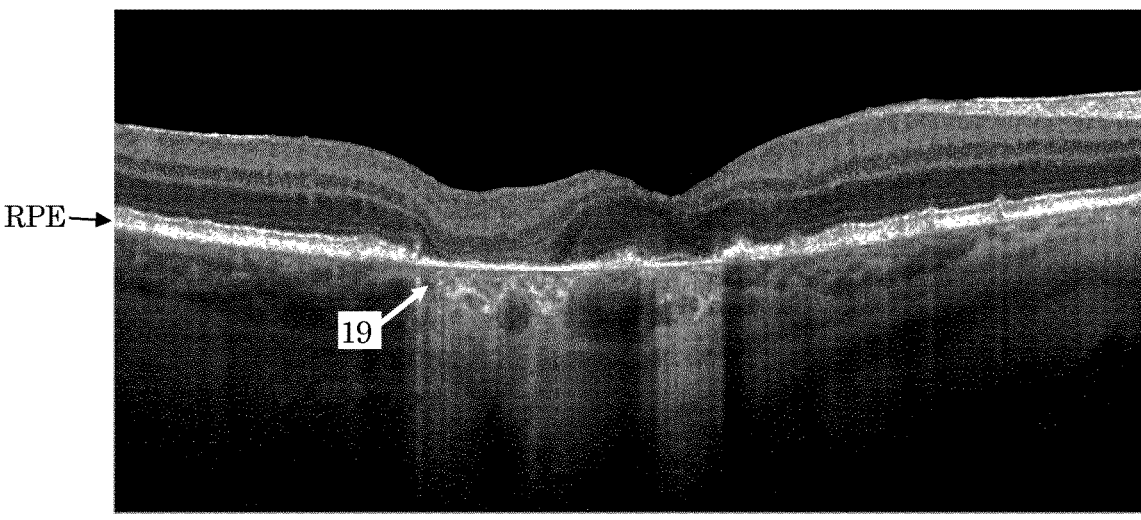
FIG. 2
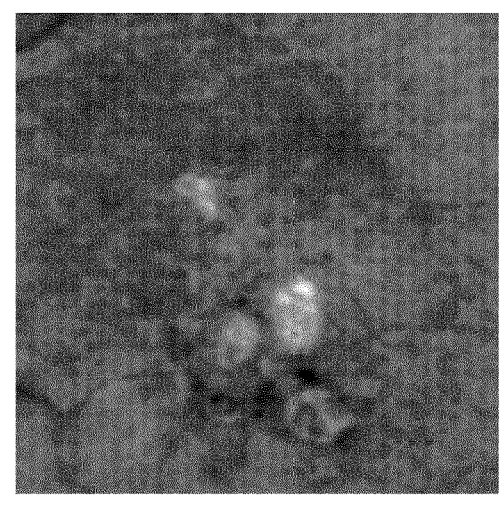  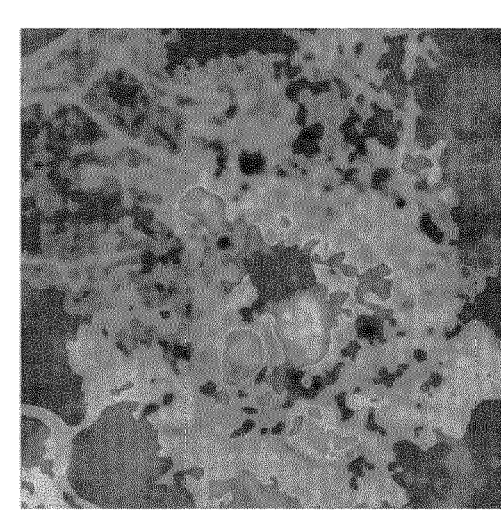
FIG. 4A                    FIG. 4B

FIG. 13

Layr1. Inner Limiting Membrane (ILM)
Layr2: (Retinal) Nerve Fiber Layer (RNFL or NFL)
Layr3: Ganglion Cell Layer (GCL)
Layr4: Inner Plexiform Layer (IPL)
Layr5: Inner Nuclear Layer (INL)
Layr6: Outer Plexiform Layer (OPL)
Layr7' Outer Nuclear Layer (ONL)
Layr8: Junction between Outer Segments (OS) and Inner Segments (IS)
Layr9: Externa/Outer Limiting Membrane (ELM/OLM)
Layr10: Retinal Pigment Epithelium (RPE)
Layr11. Bruch's Membrane (BM)

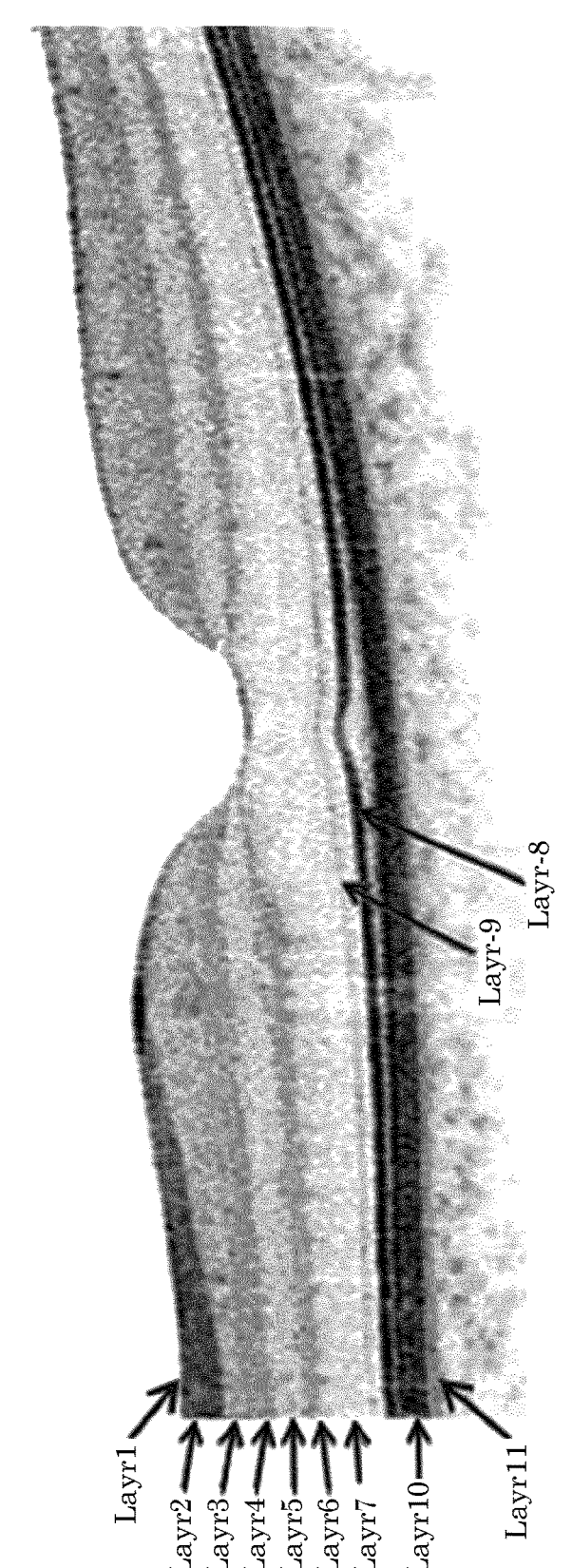

OCT *EN FACE* PATHOLOGY SEGMENTATION USING CHANNEL-CODED SLABS

PRIORITY

This application is a National Phase application under 35 U.S.C. § 371 of International Application No. PCT/EP2021/061147, filed Apr. 28, 2021, which claims priority to U.S. Provisional Application Ser. No. 63/017,574, filed Apr. 29, 2020, the contents of which are hereby incorporated by reference in their entirety.

FIELD OF INVENTION

The present invention is generally directed to a method of analyzing optical coherence tomography data to identify a target pathology. More specifically, it is directed to analyzing optical coherence tomography data to identify Geographic Atrophy (GA).

BACKGROUND

Age-related macular degeneration (AMD) is an eye disease most common in the older population and arising from damage to the macula that leads to loss of central vision. Some patients with age-related macular degeneration (AMD) develop geographic atrophy (GA), which refers to regions of the retina where cells waste away and die. Geographic Atrophy (GA) is a condition of the macula present at the advanced stages of non-exudative macular degeneration. GA has a characteristic appearance resulting from the loss of the photoreceptor layer, retinal pigment epithelium (RPE), and choriocapillaris. GA typically first appears in the parafoveal location and progresses around the fovea and then through the fovea with loss of central visual acuity. While there is currently no known treatment to effectively delay or reverse the effects of GA, characterization and monitoring macular regions affected by GA is fundamental for patient diagnosis, monitoring and management as well as for treatment research purposes.

GA appearance has been studied (e.g., using 2D topographic imaging techniques) in reflectance (color) fundus imaging, autofluorescence imaging, and more recently in Optical Coherence Tomography (OCT) imaging. GA regions are effectively visualized in OCT not by directly looking at RPE disruption, but by taking advantage of the implications this disruption has on the light transmitted through the choroid. The RPE is a very highly reflective layer for OCT signal and the increased penetration of light (OCT signal) into the choroid where atrophy occurs allows for the visualization of GA presence in en face sub-RPE images, such as may be formed by axial projection of a sub-volume (e.g., slab) of OCT data extending from the RPE (or slightly above the RPE) to below the RPE and into the choroid. The presence of GA in an OCT image may be identified as a brighter region within the en face sub-RPE image. This characteristic of GA in OCT images may be termed sub-RPE hyperreflectivity.

Quantification of GA properties that may be of value, or interesting, for monitoring this condition (such as area size or distance to the fovea center, as may be viewed in an en face sub-RPE image or other 2D frontal image) depends on the delineation or segmentation of the GA region within the macula. However, manually segmenting GA regions in OCT data is a challenging and time-consuming task.

Although sub-RPE hyperreflectivity remains a reasonable approach for visualizing GA in OCT data, the presence of GA is inferred (e.g., based on a variation in reflectivity) and not directly observed. Consequently, this approach is subject to possible difficulties arising from other factors that may also affect reflectivity, such as the presence of superficial or choroidal blood vessels that create shadows, possible retinal opacities as hyperreflective foci, or regions of increased choroid signal within intact RPE. Because of these difficulties, an en face (e.g., a frontal, planar view) image of a sub-RPE region has heretofore not been sufficient, and a careful B-scan by B-scan review of the suspected GA region has been necessary to confirm the presence of GA. A B-scan provides an axial, slice (or side) view of a region (e.g., slicing through retinal layers), and the presence of GA may be confirmed by noting a verifiable loss of the RPE layer and retina thinning or collapse.

Most common automated GA segmentation methods are based on the analysis of sub-RPE hyperreflectivity in a single sub-RPE en face image, and are subject to the difficulties and possible errors outlined above. Checking and correcting possible errors has heretofore required careful B-scan review since the singular sub-RPE en face image does not provide all needed information.

What is needed is a method for identifying GA presence that considers information from an entire OCT volume, but is as simple to use as the traditional method of using a sub-RPE en face image.

It is an object of the present invention to provide a more accurate GA detection system for use with OCT.

It is another object of the present invention to provide an OCT-based GA detection method that takes into consideration multiple types of OCT information, such as may be obtained from a combination of en face and B-scan images.

It is a further object of the present invention to provide an OCT-based system that provides an en face image representation of a combination of OCT-based data, non-OCT image data, and/or non-image data.

It is still another object of the present invention to provide a system/method that identifies/segments GA regions in an en face OCT image taking into consideration image information from different types of imaging modalities and non-image information.

SUMMARY OF INVENTION

The above objects are met in a method/system for analyzing optical coherence tomography (OCT) data to identify/segment a target pathology (e.g., geographic atrophy) in an en face image. The present invention integrates different aspects of OCT volumetric information into different image channels (e.g., color channels) of a single image to produce an improved GA detection, analysis and segmentation tool. The present method provides for better GA visualization in a single image, which may be used in a segmentation algorithm to provide a more accurate segmentation (e.g., GA segmentation), or for review and editing of segmentation results. Unlike prior art techniques, which focus on displaying and characterizing a single factor related to possible GA presence (e.g., sub-RPE reflectivity), the present approach integrates multiple different aspects of an OCT volume into additional channels (e.g., pixel/voxel channels) that may be combined to more accurately analyze and segment GA. For example, the additional information may include an analysis of, or data related to, RPE integrity or retinal thinning (e.g., thinning of specific retinal layers), which would previously have required analysis of individual B-scans.

Other objects and attainments together with a fuller understanding of the invention will become apparent and appreciated by referring to the following description and claims taken in conjunction with the accompanying drawings.

Several publications may be cited or referred to herein to facilitate the understanding of the present invention. All publications cited or referred to herein, are hereby incorporated herein in their entirety by reference.

The embodiments disclosed herein are only examples, and the scope of this disclosure is not limited to them. Any embodiment feature mentioned in one claim category, e.g. system, can be claimed in another claim category, e.g. method, as well. The dependencies or references back in the attached claims are chosen for formal reasons only. However, any subject matter resulting from a deliberate reference back to any previous claims can be claimed as well, so that any combination of claims and the features thereof are disclosed and can be claimed regardless of the dependencies chosen in the attached claims.

BRIEF DESCRIPTION OF THE DRAWINGS

In the drawings wherein like reference symbols/characters refer to like parts:

FIG. 1 shows three examples of a GA within images of three different imaging modalities.

FIG. 2 provides an example of a B-scan through a GA region.

FIG. 4A shows a sub-RPE slab projection, as may be traditionally used to identify candidate GA regions.

FIG. 4B shows a channel-coded image (multi-channel composite image) in accord with the present invention, where each image channel (e.g., color channel) embodies a different pathology-specific characteristic.

FIG. 13 shows an exemplary OCT B-scan image of a normal retina of a human eye, and illustratively identifies various canonical retinal layers and boundaries.

DESCRIPTION OF THE PREFERRED EMBODIMENTS

Figure 3:
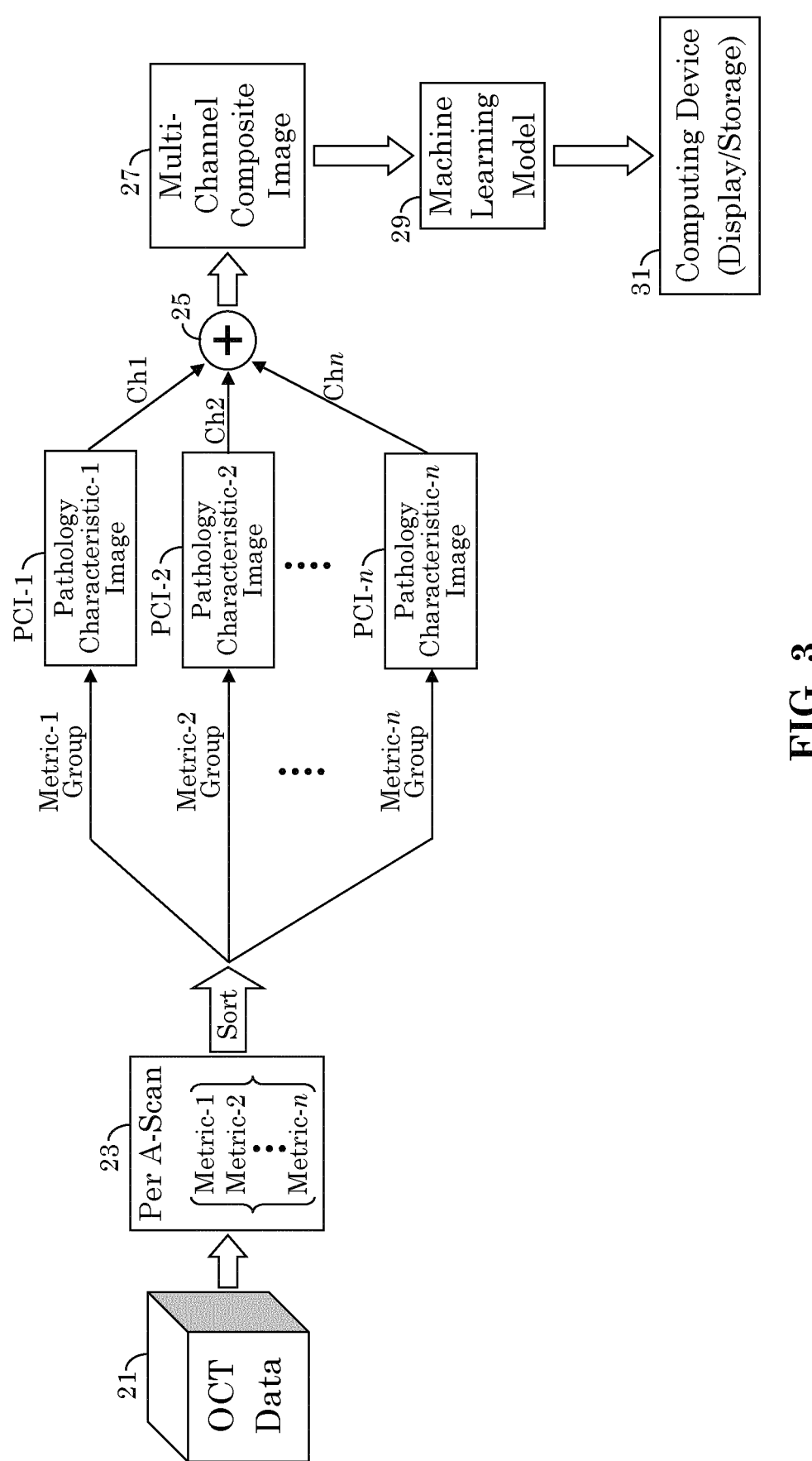
FIG. 3 illustrates an embodiment of the present invention.

Geographic atrophy (GA) refers to regions of the retina where cells waste away and die (atrophy). These regions of atrophy generally result in blind spots in a person's visual field. Consequently, monitoring and characterizing retinal regions affected by GA is fundamental for patient diagnosis and management. Various imaging modalities have proven useful in detecting and characterizing GA, such as fundus imaging (including autofluorescence and fluorescein angiography), optical coherence tomography (OCT), OCT angiography (OCTA), etc.

Fundus imaging, such as may be obtained by use of a fundus camera, generally provides a frontal planar view of the eye fundus as seen through the eye pupil. Fundus imaging may use light of different frequencies, such as white, red, blue, green, infrared, etc. to image tissue, or may use frequencies selected to excite fluorescent molecules in certain tissues (e.g., autofluorescence) or to excite a fluorescent dye injected into a patient (e.g., fluorescein angiography). A more detailed discussion of different fundus imaging technologies is provided below.

OCT is a non-invasive imaging technique that uses light waves to produce cross-section images of retinal tissue. For example, OCT permits one to view the distinctive tissue layers of the retina. Generally, an OCT system is an interferometric imaging system that determines a scattering profile of a sample along an OCT beam by detecting the interference of light reflected from a sample and a reference beam creating a three-dimensional (3D) representation of the sample. Each scattering profile in the depth direction (e.g., z-axis or axial direction) may be reconstructed individually into an axial scan, or A-scan. Cross-sectional, two-dimensional (2D) images (B-scans), and by extension 3D volumes (C-scans or cube scans), may be built up from multiple A-scans acquired as the OCT beam is scanned/moved through a set of transverse (e.g., x-axis and y-axis) locations on the sample. OCT also permits construction of a planar, frontal view (e.g., en face) 2D image of a select portion of a tissue volume (e.g., a target tissue slab (sub-volume) or target tissue layer(s) of the retina). OCTA is an extension of OCT, and it may identify (e.g., renders in image format) the presence, or lack, of blood flow in a tissue layer. OCTA may identify blood flow by identifying differences over time (e.g., contrast differences) in multiple OCT images of the same retinal region, and designating differences that meet predefined criteria as blood flow. A more in-depth discussion of OCT and OCTA is provided below.

Each imaging modality may characterize GA differently. FIG. 1 shows three examples of a GA within images of three different imaging modalities. Image 11 is a reflectance (color) fundus image and image 13 is an autofluorescence image (obtained using 2D topographic imaging techniques). Image 15 is sub-RPE, OCT, en face image. In images 11, 13, and 15, GA is identified as region 17. GA generally results in a loss or thinning of some retinal layers (e.g., the photoreceptor layer, retinal pigment epithelium (RPE), and choriocapillaris). Suspicious regions in the frontal view may be identified, at least in part, by the effects of the loss/reduction of these retinal layers caused by GA. The reduction of these layers may result in characteristic color, intensity, or texture changes in a frontal, planar view of the retina, as viewed in a fundus, OCT, and/or OCTA image. For example, in a healthy retina, these layers, especially the RPE, tend to reflect an OCT signal and limit its penetration into the retina. However, in a GA region, OCT signals tend to penetrate deeper into the retinal due to the thinning or loss of these layers, resulting in characteristic sub-RPE hyper-reflectivity, as is shown in image 15. Although this hyper-reflectivity may help identify a candidate/suspicious region that may be GA, it is not a direct detection of GA since other factor may also affect OCT signal reflectivity.

A more direct method of viewing GA is to use a B-scan, which provides a slice view of a GA region, and shows individual retinal layers. FIG. 2 provides an example of a B-scan through a GA region. As shown, GA region 19 may be identified by a thinning of the RPE and other layers, an increase in reflectivity/brightness below the RPE layer, and/or an overall thinning or collapse of the retina. Therefore, a more direct method of searching for GA is to inspect individual B-scans, but it is generally time-consuming to inspect each B-scan in a volume for the existence of GA. Consequently, a quicker method for detecting GA is to inspect a single frontal, planar view of the fundus/retina and identify suspicious regions, such as illustrate in images 11, 13, or 15 in FIG. 1, and then inspect individual B-scans (one-by-one) that traverse the suspicious regions.

GA detection, characterization, and segmentation in OCT data has traditionally been done in sub-RPE en face slabs/images by analyzing the increased signal in the choroid derived from RPE disruptions. Examples of this approach may be found in Qiang Chen et al. "Semi-automatic geographic atrophy segmentation for SD-OCT images," *Biomed. Opt. Express* 4, 2729-2750 (2013), and in Sijie Niu et al., "Automated geographic atrophy segmentation for SD-OCT images using region-based C-V model via local similarity factor," *Biomed. Opt. Express* 7, 581-600 (2016). This approach, however, is subject to possible difficulties and limitations by any of a number of factors that may affect the observed signal (e.g., reflectivity) within a sub-RPE en face image. Consequently, commercial automated GA segmentation tools based on this approach have been known to provide less than optimal results, requiring a subsequent B-scan review to confirm possible GA presence.

A different approach is described in Ji Z. et la., "Retinal Layers: A Deep Voting Model for Automated Geographic Atrophy Segmentation in SD-OCT Images," *Transl Vis Sci Technol.,* 2018;7(1). This approach is based on Neural Networks and takes individual B-scans directly for GA segmentation. However, this process can be complicated due to the need for annotating individual B-scans, and may produce discontinuous results in neighboring B-scans. Furthermore, this approach does not solve the problem of needing a subsequent B-scan by B-scan to confirm the GA segmentation results.

Thus, OCT-based, GA characterization methods have traditionally focused in the analysis of sub-RPE reflectivity in en face images, leaving out important information, such as direct analysis of RPE integrity or retinal thinning. In order to consider such information, additional review of multiple images (e.g., from different imaging modalities) or multiple OCT B-scans has previously been needed.

The present invention collects GA characteristic information from multiple different image views (and/or imaging modalities), and combines/incorporates the information into a single, customized, frontal image of the retinal that permits more accurate identification GA regions by presenting multiple sources of information. That is, the present invention presents these several sources of information in a single image that can be used to manually judge the presence of GA or used in automated or semi-automated GA segmentation tools. The different characteristic information may be stored (or coded) into additional channels (e.g., color channels) of the image, such as on a pixel (or voxel) basis. The combination of the different characteristics (e.g., GA-related information) into different channels of a single image allows for a more accurate and effective characterization and segmentation of GA regions.

In summary, a first exemplary implementation of the present invention uses, for example, a set of en face images (topographic projections from an OCT volume forming a frontal-view, 2D image) with different definitions, and stacks their information in different channels (e.g., color channels) of a single image to generate channel-coded images where different properties that characterize the presence of GA (or other targeted pathology) are encoded in the different channels. A preliminary step may be the segmentation of a set of retina layers within the OCT volume to assist in the en face creation (e.g., assist in selecting layers that may be characteristic to (e.g., associated with) the target pathology and used to define the slabs from which the en face images are to be created). Then, a set of different en face images are created using the segmented layers and/or set of slab definitions. The en face images may then be stacked (or combined) in different channels (e.g., pixel/voxel color channels). The resulting set of stacked slabs may be used to visualize GA (or other specific pathology) and other retina landmarks (e.g., such as if three distinct slabs are stacked in place of respective red, green, blue (RGB) color channels of a typical color image), and/or used for automated segmentation of GA using the information encoded in the different channels.

FIG. 3 illustrates an embodiment of the present invention. A first step is to acquire OCT data 21 (e.g., one or more data volumes of the same region of a retina). Optionally, the OCT data 21 may be submitted to a retinal layer segmentation process. As part of, or in addition to, this process, each A-scan in OCT data 21 is processed to extract a series of metrics 23, where each metric is selected to measure (or emphasize, such as by weight) a characteristic of a specific target pathology, e.g., GA. That is, the extracted metrics may be associated with the same pathology type such that each metric provides a different marker for the same pathology type. The extracted metrics are sorted, or otherwise collected, into corresponding metric groups (metric-1 group to metric-n group), optionally with a one-to-one corresponding. The OCT data 21 may include OCT structural data and/or OCTA flow data, and the extracted metrics may include OCT-based metrics extracted from the OCT structural data, such as retinal layer thicknesses, distances of a specific A-scan to a specific retinal structure (e.g., distance to the fovea center), layer integrity (e.g., the loss of a specific layer), sub-RPE reflectivity, inner RPE reflectivity, overall retinal thickness, and/or the optical attenuation coefficient (OAC).

The optical attenuation coefficient (OAC) is an optical property of a medium that determines how the power of a coherent light beam propagating through the (e.g., turbid) medium (e.g., tissue) is attenuated along its path due to scattering and absorption. The irradiance (power per unit area) of the coherent light beam that propagates through a (e.g., homogeneous) medium is given by Lambert-Beer's law: $L(z)=L_0 e^{-\mu z}$, where $L(z)$ is the irradiance of the beam after traveling through the medium over a distance z, $L_0$ is the irradiance of the incident light beam and μ is the optical attenuation coefficient. Large attenuation coefficients result in a quick and exponential decline of the irradiance of the coherent light beam with depth. Because the OAC is an optical property of the medium, determining the OAC provides information on the composition of this medium. Applicants propose that providing the OAC (per A-scan) as one of the extracted metrics may be beneficial identify specific pathologies (e.g., GA), particularly since it can be indicative of the current state (e.g., light attenuating state) of tissued at specific A-scan positions. An example of how the OAC may be determined/calculated is provided in "Depth-Resolved Model-Based Reconstruction of Attenuation Coefficients in Optical Coherence Tomography", by K. A. Vermeer et al., *Biomedical Optics Express,* Vol. 5, Issue 1, pp. 322-337 (2014). A discussion of previous applications of OAC may be found in "In Vivo Tissue Injury Mapping Using Optical Coherence Tomography Based Methods", by Utka Baran et al., *Applied Optics,* Vol. 54, No. 21, Jul. 20, 2015.

The extracted metrics may also include OCTA-based metrics extracted from the OCTA flow data, such as flow measures (e.g., blood flow) at locations within one or more layers (e.g., Choriocapillaris, Satller's layers, Haller's layer, etc.) and distances from the flow data to the fovea center, etc. In this manner, each metric group may describe a different pathology characteristic, and multiple metric groups (metric-1 group to metric-n group) may be used to define multiple corresponding pathology characteristic images (PCI-1 to PCI-n), each highlighting a different pathology characteristic. Each pathology-characteristic image PCI-1 to PCI-n may define an en face image. The different pathology characteristic images may then be used to define a different pixel channel (Ch1 to Chn) and combined (as illustrated by block 25) to define a multi-channel composite image (e.g. a channel-coded image) 27. Optionally, the multi-channel composite image 27 may be of lower dimension than OCT data 21, such as an en face image (and/or B-scan image), where each pixel location of the composite image 27 is based a corresponding A-scan location of the OCT data 21. In this manner, each metric may be used as the bases for a different, corresponding channel in composite image 27. The resultant multi-channel composite image 27 may then be submitted to a machine learning model 29 trained to identify the target pathology (e.g., GA) based on the pathology-characteristic data (e.g. metric groups) embodied in the individual image channels. The identified pathology may then be displayed or stored for future processing in a computing device 31.

As an example, a proof of concept implementation used three metric groups to define three different slabs (pathology-characteristic images) assigned to the three typical red, green, and blue (RGB) color channels of an image. It is to be understood that a channel-coded image may optionally have more (or fewer) channels. FIG. 4A shows a sub-RPE slab projection, as may be traditionally used to identify candidate GA regions, and FIG. 4B shows a channel-coded image (multi-channel composite image) in accord with the present invention, where each image channel (e.g., color channel) embodies a different pathology-specific characteristic (embodies a different metric group). In the present example, the red channel (or medium gray in a black-and-white, monochrome image) comprises sub-RPE reflectivity data. To gather metrics for the red channel, a 300 μm slab is defined outer to the RPE layer and into the choroid vicinity, with surface limits specified between the RPE layer plus offsets of 50 μm and 350 μm, respectively. The OCT signal within this slab is filtered for noise removal and then processed so the signal at each A-scan location has a constantly decreasing function with increase of depth, filling "valleys" in the signal. That is, for each particular pixel in an A-scan, the value is set to be as the highest value recorded in such A-scan from the considered pixel to increasing depths within the defined slab limits. This operation is set to eliminate lower value signal originated from the presence of choroidal blood vessels. The resulting data is projected into an en face image by averaging the pixel values within the slab limit definition for each A-scan. The resulting values of the en face image are then normalized to be in the range between 0 and 1. The goal of this slab is to characterize the increased reflectivity present in the choroid in GA regions.

In the present example, the green channel (e.g., light gray in a black-and-white, monochrome image) encompasses inner RPE reflectivity. To gather metrics for the green channel, a 20 μm slab is defined inner to the RPE-Fit layer (an estimation of the Bruch's membrane curvature set at the level of the RPE centerline), with surface limits specified between the RPE-Fit layer and offsets of minus 50 μm and minus 30 μm, respectively. The OCT signal within this slab is filtered for noise removal and then processed so the signal at each A-scan location has a constantly increasing function with increase of depth, filling "valleys" in the signal. That is, for each particular pixel in an A-scan, the value is set to be as the highest value recorded in such A-scan from the inner slab limit up to the considered pixel. This operation is set to eliminate lower value signal caused by shadowing of higher opacity structures (for example, blood vessels, drusen or hyperreflective foci) in an otherwise intact RPE. The resulting data is projected into an en face image by averaging the pixel values within the slab limit definition for each A-scan. The resulting values of the en face image are normalized to be in the range between 0 and 1. The goal of this slab is to characterize the lower reflectivity in locations with photoreceptor and RPE loss.

In the present example, the blue channel (or dark gray in a black-and-white, monochrome image) encompasses retinal thickness. To gather metrics for the blue channel, the distance between the ILM layer and the RPE-Fit layer (retinal thickness) is measured for each A-scan location and projected into an en face image. The recorded values are then scaled in an inverted linear operation to take values from 0 to 1 so that a retinal thickness of 100 μm takes the value of 1 and a thickness of 350 μm takes the value of 0. The goal of this slab is to characterize the localized regions of retinal thinning and collapse characteristic of GA presence.

Figure 5:
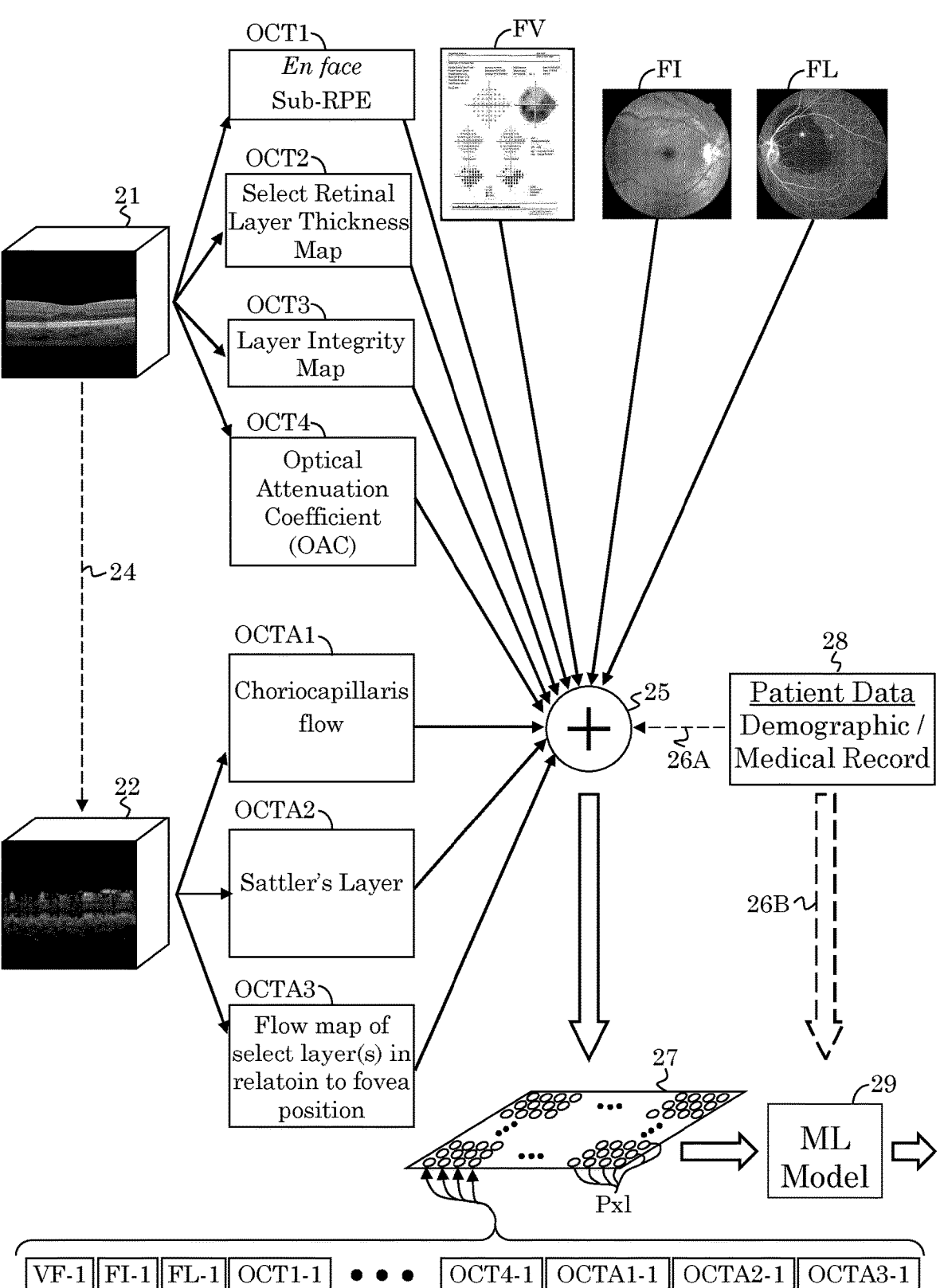
FIG. 5 illustrates an alternate embodiment where the multi-channel composite image is comprised of images of different imaging modalities and optionally of non-image data.

FIG. 5 illustrates an alternate embodiment where the multi-channel composite image (i.e., color-coded or monochrome coded image) 27 is comprised of images of different imaging modalities and optionally of non-image data. In the present embodiment, OCT data 21 is acquired, or otherwise accessed. OCT data 21 may be a cube scan comprised of multiple A-scans and/or accessed B-scans, and may optionally include multiple scans of the same region separated in time. In this case, OCTA data 22 may be determined from OCT data 21, as indicated by dotted arrow 24. Alternatively, OCTA data 22 may be acquired/accessed separately. A series of metrics may then be extracted from each OCT data 21 and OCTA data 22, and a set of pathology characteristic images (or maps) may be defined from the extracted metrics (e.g., metric groups). In the present illustration, images OCT1 to OCT4 are defined based on metrics extracted from OCT data 21, and images OCTA1 to OCTA3 are defined based on metrics extracted from OCTA data 22. For example, images OCT1 to OCT4 may respectively represent an en face sub-RPE image, a thickness map of select layers (e.g., the photoreceptor layer, retinal pigment epithelium (RPE), and/or choriocapillaris, and may further locate the fovea, such as by use of an automated fovea location algorithm), a layer integrity map (e.g., such as would typically be determined from multiple B-scan), and an OAC map. In the present example, images OCTA1 to OCTA3 may respectively represent an en face OCTA image of choriocapillaris flow, an image of Sattler's layer (e.g., situated between the Bruch's membrane, choriocapillaris, and Haller's layer below, and the suprachoroidea above), and/or a flow map of other select layers in relation to the fovea position.

As is explained above, GA may result in a progressive loss of vision, particularly central vision. However, GA may start with loss of vision outside the central area, and progress toward the center over time. Thus, it is advantageous to incorporate information from visual field test results FV. A visual field test is a method of measuring an individual's entire scope of vision, e.g., their central and peripheral (side) vision. Visual field testing is a way to map the visual fields of each eye individually and can detect blind spots (scotomas) as well as more subtle areas of dim vision. A campimeter, or "perimeter," is a dedicated machine/device/system that applies a visual field test to a patient. A more in-depth discussion of perimeters and visual field testing is provided below. All, or select parts of a visual field test (such as the VF gray scale or numerical gray scale mapped to corresponding retinal locations) may be incorporated into the present multi-channel composite image 27.

Additional imaging modalities may include one more types of fundus image FI (e.g., white, red, blue, green, infrared, autofluorescence, etc.) and fluorescein angiography image(s) FL.

Each of the above-described different data types may represent a different pathology-characteristic image, and be combined, as illustrated by block 25, to define a multi-channel composite image 27. As illustrated, each pixel (illustrated as circles Px1) may include data (e.g., metrics) from each of the above-described sources. For example, each pixel may define (for a corresponding retina position) a data record comprised of multiple data fields, one per incorporated pathology-characteristic image. Each pixel may include a visual field test data field (VF-1), a fundus image data field (FI-1), a fluorescein angiography image data field (FL-1), an OCT structural data field (OCT1-1, OCT2-1, OCT3-1, and OCT1-4) from each corresponding OCT structure image, and an OCTA flow data field (OCTA1-1, OCTA2-1, and OCTA3-1) from each corresponding OCTA flow image.

The composite image 27 may then be submitted to a machine learning model 27 for processing or training, as described below. As in the embodiment of FIG. 5, the output from the machine learning model 27 may be submitted to a computing device (not shown) for display or storage. Optionally, non-image data 28 may also be submitted to the machine model 29 for processing, either indirectly via dotted arrow 26A or directly via dotted block arrow 26B. That is, non-image data 28 may optimally be incorporated into the composite image 27 via block 25. The non-image data 28 may include patient demographic data (e.g., age, ethnic group, etc.) and/or medical history data (e.g., previously prescribed medication(s) and diagnosed ailments relevant to the pathology being sought, etc.) such as may be obtained from an electronic medical record (EMR) system.

The proof of concept application of the present invention implements machine learning model 29 as a neural network architecture trained for automated segmentation of GA region(s) in composite images 27 (e.g., in generated channel-coded images). A general discussion of neural networks is provided below. All the accessed images (and/or maps) used to define a composite image 27 may be normalized and resized to 256×256×3 pixels. Each image is then split into nine overlapping patches with pixel size 128×128×3 with 64 pixels overlap (50%) in both directions.

Figure 6:
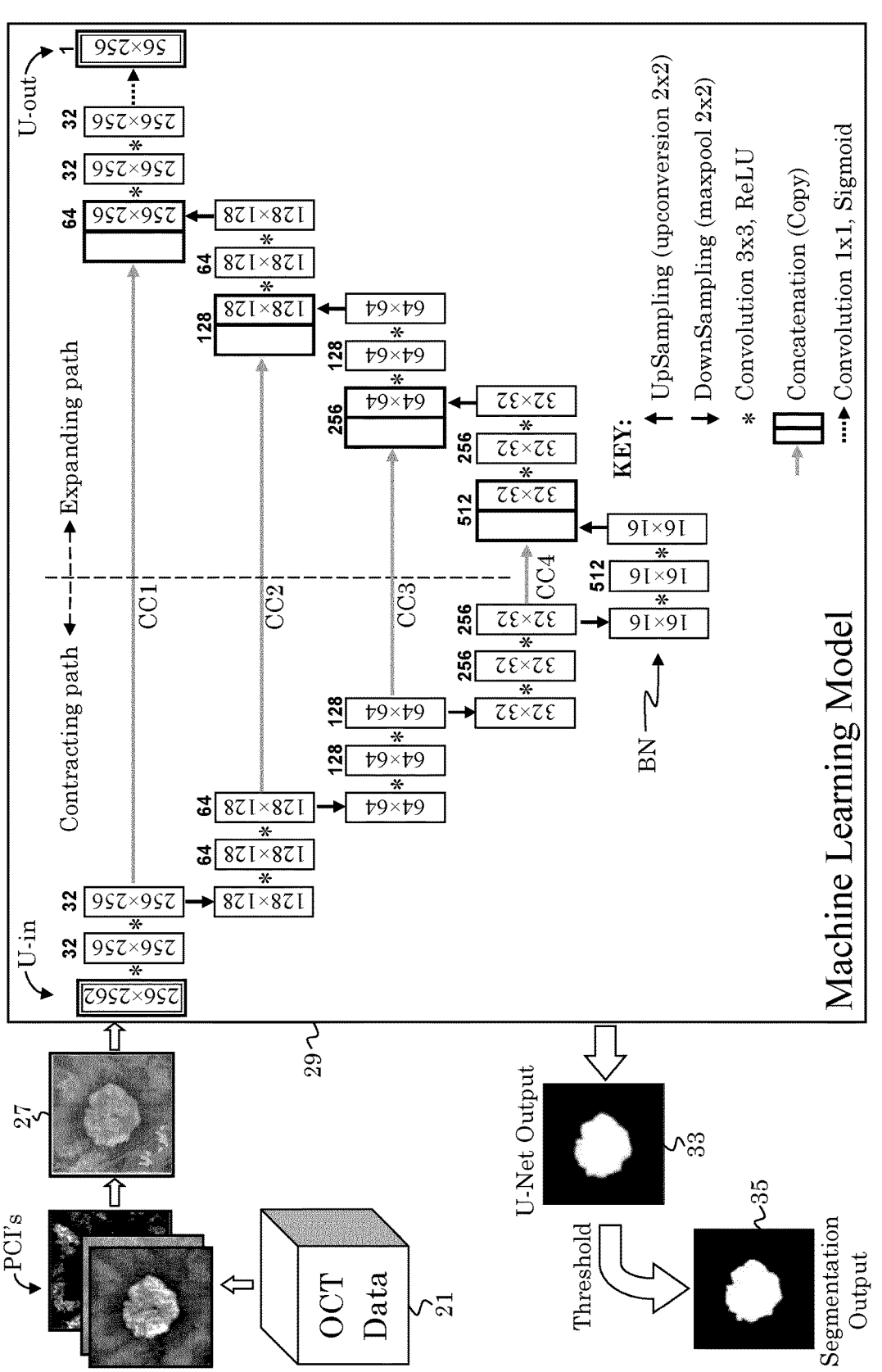
FIG. 6 illustrates a general workflow of the present invention, including the U-net architecture of the proof of concept implementation.

FIG. 6 illustrates a general workflow of the present invention, including the U-net architecture of the proof of concept implementation. As shown, OCT Data 21 is accessed/acquired and multiple pathology characteristic images PCI's are defined from the OCT data 21, as described above. For example, the pathology characteristic images PCI's may include a sub-RPE reflectivity image, an inner RPE reflectivity image, Retinal thickness, and/or optical attenuation coefficient (OAC) as described above in reference to FIGS. 3 and 4. Optionally, other pathology characteristic image may also be used, such an en face images/maps of specific retinal layer thicknesses or layer integrity, OCTA flow images (such as flow at, or within the vicinity of, the choriocapillaris), an/or other pathology characteristic data as described above in reference to FIG. 5. the pathology characteristic images are then combined into a different (e.g., color or monochrome value) channels of a channel-coded image 27, which is then submitted to machine learning model 29, which is herein implemented using a U-Net architecture. A discussion of a U-Net architecture is provided below.

In the present exemplary U-Net architecture, the contracting path consist of four convolutional neural networks (CNN) blocks. Each CCN block in the contracting path may include two (e.g., 3×3) convolution, as indicated by the asterisk symbol "*", and activation function (e.g., a rectified linear (ReLU) unit), optionally with batch normalization. The output of each CNN block in the contracting path is downsampled, such as by 2×2 max pooling, as indicated by a downward arrow. The output of the contracting path feeds into the bottleneck BN, which is here shown to consists of two convolutional layers (e.g., with batch normalization and optional 0.5 dropout). The the expansive/expanding path follows the bottleneck BN, and here consists of five CNN blocks. In the expanding path, the output of each block provides transposed convolution (or deconvolution) to upsample (e.g., upconvert) the image/information/data. In the present example, the upconversion is characterized by a 2×2 kernel (or convolution matrix), as indicated by an upward arrow. Copy-and-crop links CC1 to CC4 between corresponding downsampling and upsampling blocks copy the output of one downsampling block and concatenate it to the input of its corresponding upsampling block. At the end of the expanding path, the output of the last upsampling block is submitted to another convolution operation (e.g., 1×1 output convolution), as indicated by a dotted arrow, before producing its output U-out. For example, the neural network may have multiple features per pixels right before reaching the 1×1 output convolution, but the 1×1 convolution combines these multiple features into a single output value per pixel, on a pixel-by-pixel level.

A combination of binary cross entropy and dice coefficient loss was used for training. 'Icing on the Cake' was used on the last layer to fine-tune the model. 'Icing on the Cake' is a method where only the final layer is (re)trained after ordinary training is done. Training used 250 macular cubes (58 of pixel sizes 512×128×1024; and 192 of pixel sizes 200×200×1024) obtained from 155 patients using CIRRUS™ HD-OCT 4000 and 5000 (ZEISS, Dublin, Calif.).

Experts manually drew GA outline segmentations in en face images, looking at both hyper-reflectivity underneath the RPE and possible RPE disruption in the en face images and B-scans available. For each macular cube, a 3-channel en face image was generated as explained above (e.g., in reference to FIGS. 3 and 4A). The training and testing sets of custom-generated en face images were comprised of 225 eyes (187 containing GA; 19 containing drusen with no GA; and 19 from healthy subjects) and 25 eyes (11 containing GA, 5 containing drusen with no GA; and 9 from healthy subjects) respectively.

In operation, the trained U-Net outputs a GA segmentation 33 based on a channel-coded in image 21, as illustrated in FIG. 6. The output GA segmentation 33 may be submitted to a threshold operation (and other known segmentation cleaning operations) to produce a segmentation output 35.

Figure 7:
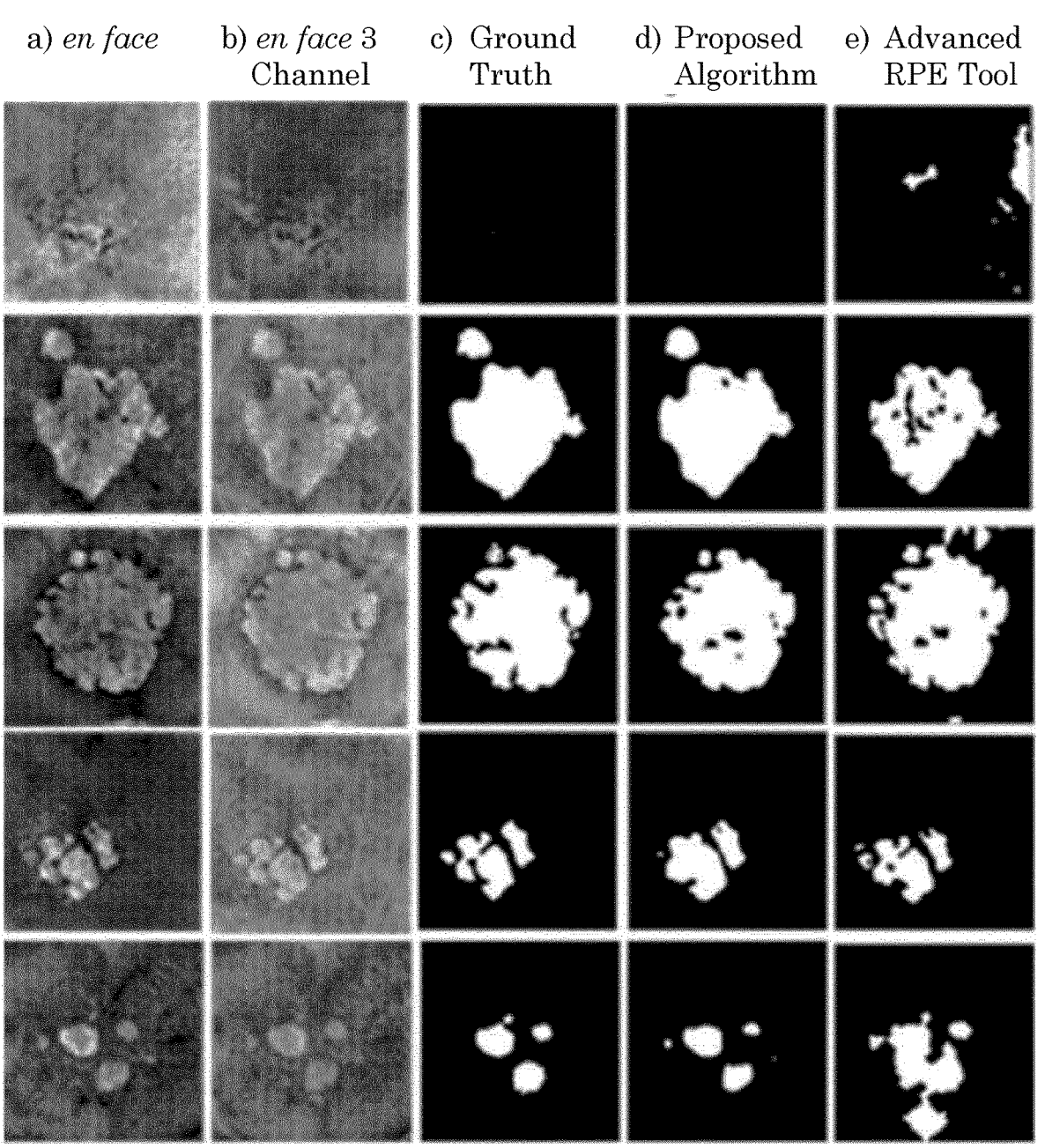
FIG. 7 shows qualitative results of the present proof of concept implementation.
Figure 8:
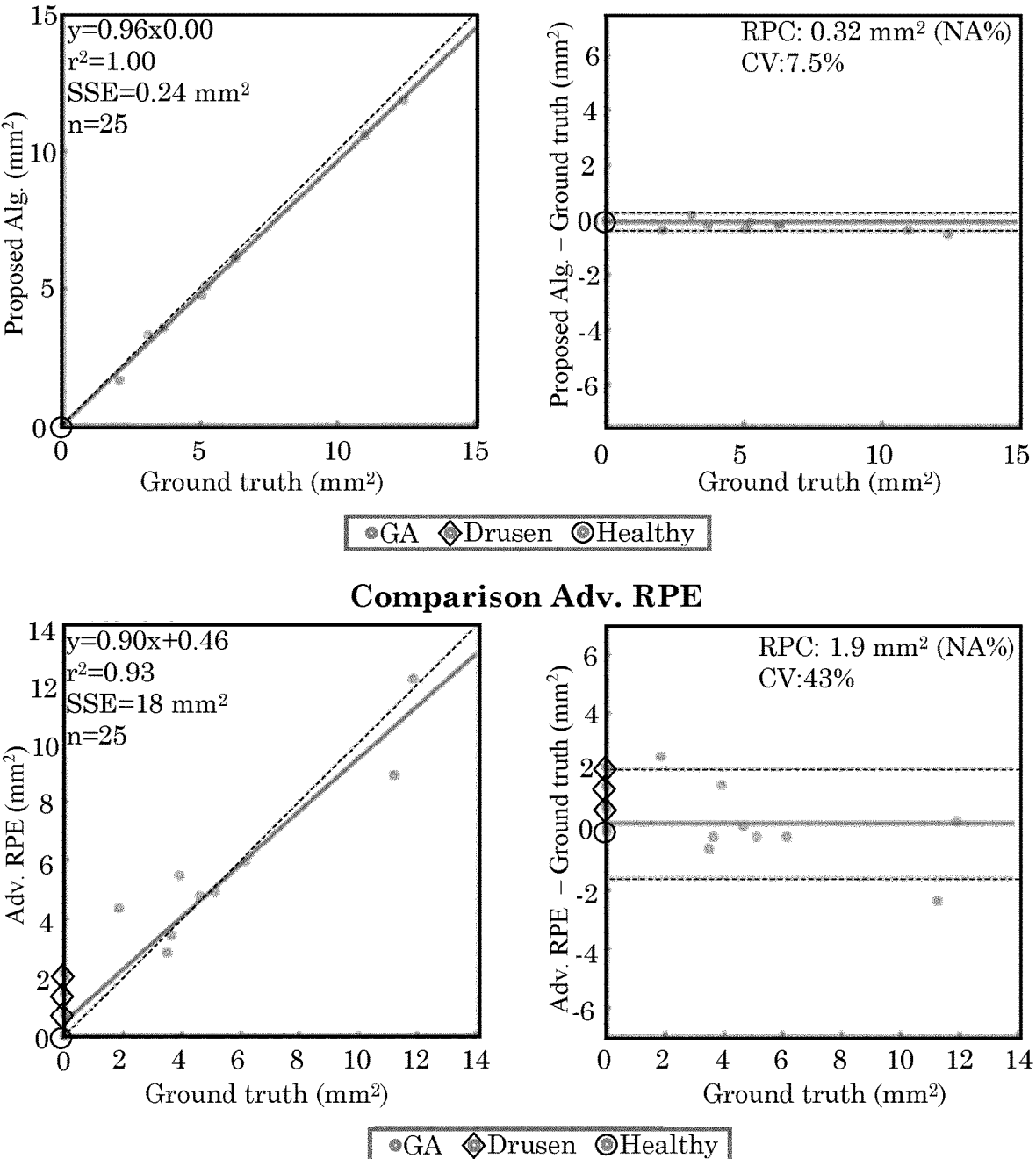
FIG. 8 shows quantitative measurements of the present proof of concept implementation.

Segmentations by the present algorithm in the test set were compared with the manual markings using qualitative and quantitative measurements (e.g., area, Bland-Altman and Pearson's correlation). FIG. 7 shows qualitative results of the present proof of concept implementation (e.g., the presently proposed algorithm), and FIG. 8 shows quantitative measurements of the present proof of concept implementation. In FIG. 7, column a) shows an obtained OCT en face image, column b) shows a generated 3 channel-coded image for input to the present trained U-Net machine model, column c) shows the ground truth images (i.e., the human expert annotated GA region, column d) shows the output produced by the presently proposed algorithm, and column e) shows the output from the "Advanced RPE Analysis" tool available in current CIRRUS™ HD-OCT review software. As illustrated in FIG. 8, the absolute and fractional area differences between GA regions generated by the proposed algorithm and the expert manual markings were 0.11±0.17 mm2 and 5.51±4.7% as opposed to 0.54±0.82 mm2 and 25.61±42.3% for the Advanced RPE Analysis tool. The inference time was 1183 ms per en face image using an Intel® i7@2.90GHz CPU. Correlations of GA areas generated by the proposed algorithm with the expert manual markings and GA areas generated by the Advanced RPE Analysis tool with the manual markings were 0.9996 (p-value<0.001) and 0.9259 (p-value<0.001) respectively. The Bland-Altman plot between the manual markings and the segmentations generated using proposed algorithm showed stronger agreement than the segmentations generated using the existing Advanced RPE analysis tool.

Figure 9:
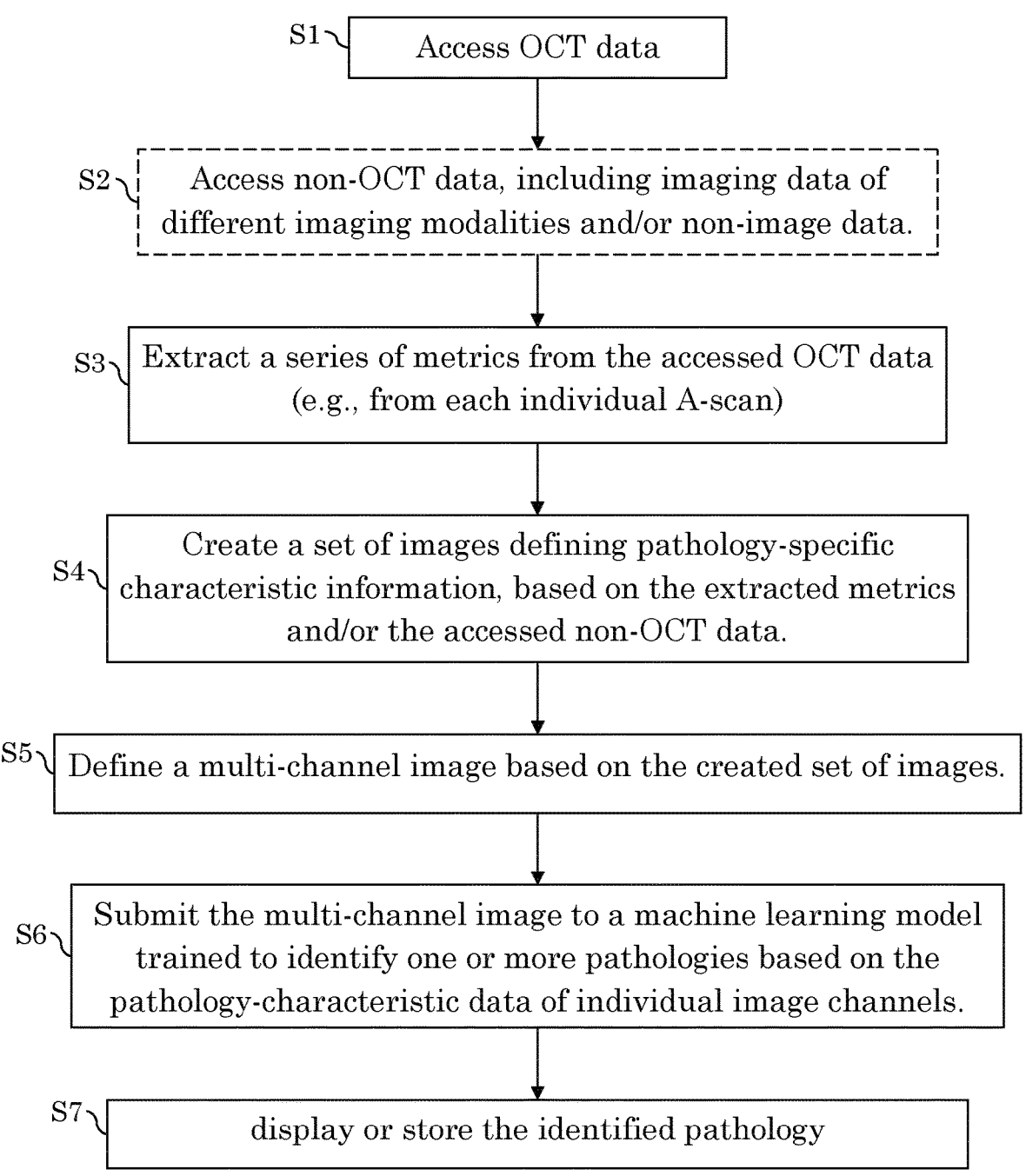
FIG. 9 provides a summary overview of the present invention.

FIG. 9 provides a summary overview of the present invention. The present method for analyzing optical coherence tomography (OCT) data to identify a specific pathology, such as GA, may begin with accessing the OCT data (step S1), which may include OCTA data (or OCTA data may be derived from the accessed OCT data). That is, the accessed data (e.g., captured using an OCT system, read from a data store of previously captured/processed OCT data, etc.) may include OCT structural data and OCTA flow data.

Optionally, the present method may further include accessing non-OCT-based data (step S2), including imaging data of imaging modalities different than OCT. For example, the present system may access fundus image(s), fluorescein angiography image(s), visual field test map(s), and/or non-image data (e.g., patient demographic data, illness and medication history, etc.).

In step S3, a series of metrics are extracted from the accessed OCT data (and optionally from the other data extracted in step S2). The extracted metrics may include OCT-based metrics extracted from the OCT structural data and/or OCTA-based metrics extracted from the OCTA flow data. The metrics may be targeted to specific retinal layers, and/or may include information related to distances from a current position to a predefined retinal landmark. For example, the metrics may be extracted from each individual A-scan, and the metrics may include information of a current A-scan's position (or an axial position within the current A-scan) relative to the fovea, to a specific retinal layer region, or to other retinal landmark.

In step S4, a set of images are created, where each image defines, or highlights, pathology-specific (e.g., GA) characteristic information. That is, the created images may characterize (e.g., be associated with) the same pathology type. The created images may be based on the extracted metrics, or on any of the other data types accessed in step S2. For example, the extracted metrics from each A-scan may be sorted into corresponding metric groups (e.g., with a one-to-one correspondence), and a different image may be created based on each respective metric group. The images created from OCT-based data may be en face images, whereas the images created from non-OCT-based data may be planar, frontal-view images. For example, the created images may include en face images of sub-RPE reflectivity, inner RPE reflectivity, en face retinal thickness, choriocapillaris flow, image of Sattler's layer, Haller's layer, as well as include fundus images (e.g., white light, red light, blue light, green light, infrared light, autofluorescence light, etc.), fluorescein angiography image(s), visual field test maps, and/or a 2D distribution of non-image data (e.g., patient demographic data).

In step S5, a multi-channel image based on the set of images is defined. For example, the multi-channel image may define multiple "color" channels per pixel where each created image defines a separate color channel. In other words, the multi-channel image may include multiple image channels respectively based on multiple imaging modalities. Optionally, a combination of created images may define a single color channel.

In step S6, The defined multi-channel image is submitted to a machine learning model (e.g. a neural network having a U-Net architecture) trained to identify one or more pathologies (preferably trained to identify the target pathology) based on the pathology-characteristic data of individual image channels. The machine model may identify the target pathology by outlining/segmenting the pathology on an en face OCT image. That is, the individual image channel locations may be mapped to a general OCT en face image, and identified regions of the multi-channel image where the pathology is present (based on a combination of pathology-characteristic data provided by the individual channels of each pixel of the multi-channel image) may be mapped back to the general OCT en face image.

In step S7, the identified pathology is displayed or stored in a computing device for future reference.

Hereinafter is provided a description of various hardware and architectures suitable for the present invention.

Visual Field Test System

Figure 10:
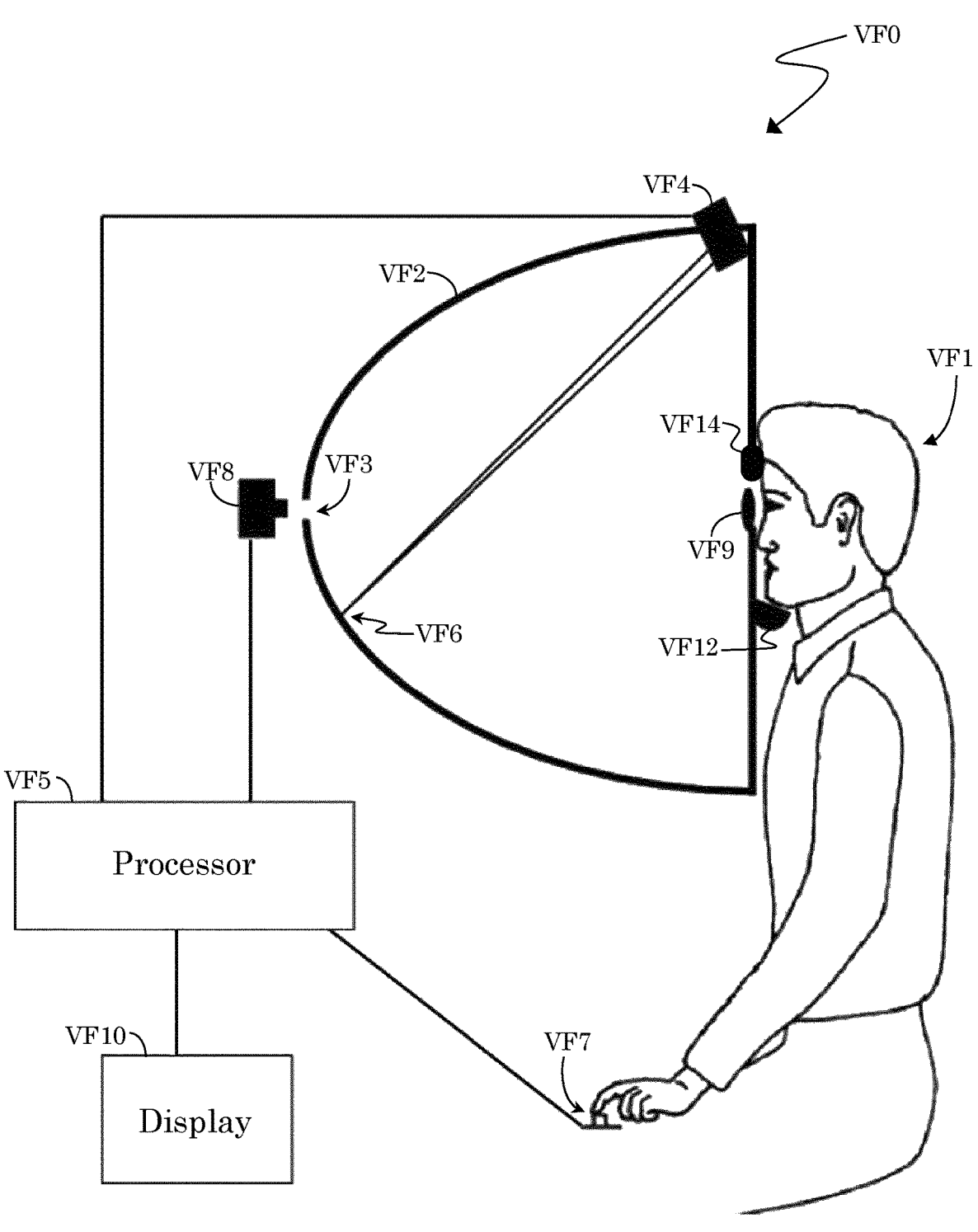
FIG. 10 illustrates an example of a visual field test instrument (perimeter) for testing a patient's visual field.

The improvements described herein may be used in conjunction with any type of visual field tester/system, e.g., perimeter. One such system is a "bowl" visual field tester VF0, as illustrated in FIG. 10. A subject (e.g., patient) VF1 is shown observing a hemispherical projection screen (or other type of display) VF2 generally shaped as a bowl, for which the tester VF0 is so termed. Typically, the subject is instructed to fixate at a point at the center of the hemispherical screen VF3. The subject rests his/her head on a patient support, which may include a chin rest VF12 and/or a forehead rest VF14. For instance, the subject rests his/her head on the chin rest VF12 and places his/her forehead against the forehead rest VF14. Optionally, the chin rest VF12 and the forehead rest VF14 may be moved together or independently of one another to correctly fixate/position the patient's eye, e.g., relative to a trial lens holder VF9 that may hold a lens through which the subject may view screen VF2. For example, the chin rest and headrest may move independently in the vertical direction to accommodate different patient head sizes and move together in the horizontal and/or vertical direction to correctly position the head. However, this is not limiting, and other arrangements/movements can be envisioned by one skilled in the art.

A projector, or other imaging device, VF4 under control of a processor VF5 displays a series of test stimuli (e.g., test points of any shape) VF6 onto the screen VF2. The subject VF1 indicates that he/she sees a stimulus VF6 by actuating a user input VF7 (e.g., depressing an input button). This subject response may be recorded by processor VF5, which may function to evaluate the visual field of an eye based on the subject's responses, e.g., determine the size, position, and/or intensity of a test stimulus VF6 at which it can no longer be seen by the subject VF1, and thereby determine the (visible) threshold of the test stimulus VF6. A camera VF8 may be used to capture the gaze (e.g., gaze direction) of the patient throughout the test. Gaze direction may be used for patient alignment and/or to ascertain the patient's adherence to proper test procedures. In the present example, the camera VF8 is located on the Z-axis relative to the patient's eye (e.g. relative to trial lens holder VF9) and behind the bowl (of screen VF2) for capturing live images(s) or video of the patient's eye. In other embodiments, this camera may be located off this Z-axis. The images from the gaze camera VF8 can optionally be displayed on a second display VF10 to a clinician (who may also be interchangeably referred to herein as a technician) for aid in patient alignment or test verification. The camera VF8 may record and store one or more images of the eye during each stimulus presentation. This may lead to a collection of anywhere from tens to hundreds of images per visual field test, depending on the testing conditions. Alternatively, the camera VF8 may record and store a full length movie during the test and provide time stamps indicating when each stimulus is presented. Additionally, images may also be collected between stimulus presentations to provide details on the subject's overall attention throughout the VF test's duration.

Trial lens holder VF9 may be positioned in front of the patient's eye to correct for any refractive error in the eye. Optionally, the lens holder VF9 may carry or hold a liquid trial lens (see for example U.S. Pat. No. 8,668,338, the contents of which are hereby incorporated in their entirety by reference), which may be utilized to provide variable refractive correction for the patient VF1. However, it should be noted that the present invention is not limited to using a liquid trial lens for refraction correction and other conventional/standard trial lenses known in the art may also be used.

In some embodiments, one or more light sources (not shown) may be positioned in front of the eye of the subject VF1, which create reflections from ocular surfaces such as the cornea. In one variation, the light sources may be light-emitting diodes (LEDs).

While FIG. 10 shows a projection type visual field tester VF0, the invention described herein may be used with other types of devices (visual field testers), including those that generate images through a liquid crystal display (LCD) or other electronic display (see for example U.S. Pat. No. 8,132,916, hereby incorporated by reference). Other types of visual field testers include, for example, flat-screen testers, miniaturized testers, and binocular visual field testers. Examples of these types of testers may be found in U.S. Pat. No. 8,371,696, U.S. Pat. No. 5,912,723, U.S. Pat. No. 8,931,905, U.S. designed Pat. D472637, each of which is hereby incorporated in its entirety by reference.

Visual field tester VF0 may incorporate an instrument-control system (e.g. running an algorithm, which may be software, code, and/or routine) that uses hardware signals and a motorized positioning system to automatically position the patient's eye at a desired position, e.g., the center of a refraction correction lens at lens holder VF9. For example, stepper motors may move chin rest VF12 and the forehead rest VF14 under software control. A rocker switch may be provided to enable the attending technician to adjust the patient's head position by causing the chin rest and forehead stepper motors to operate. A manually moveable refraction lens may also be placed in front of the patient's eye on lens holder VF9 as close to the patient's eye as possible without adversely affecting the patient's comfort. Optionally, the instrument control algorithm may pause perimetry test execution while chin rest and/or forehead motor movements are under way if such movements would disrupt test execution.

Fundus Imaging System

Two categories of imaging systems used to image the fundus are flood illumination imaging systems (or flood illumination imagers) and scan illumination imaging systems (or scan imagers). Flood illumination imagers flood with light an entire field of view (FOV) of interest of a specimen at the same time, such as by use of a flash lamp, and capture a full-frame image of the specimen (e.g., the fundus) with a full-frame camera (e.g., a camera having a two-dimensional (2D) photo sensor array of sufficient size to capture the desired FOV, as a whole). For example, a flood illumination fundus imager would flood the fundus of an eye with light, and capture a full-frame image of the fundus in a single image capture sequence of the camera. A scan imager provides a scan beam that is scanned across a subject, e.g., an eye, and the scan beam is imaged at different scan positions as it is scanned across the subject creating a series of image-segments that may be reconstructed, e.g., montaged, to create a composite image of the desired FOV. The scan beam could be a point, a line, or a two-dimensional area such a slit or broad line. Examples of fundus imagers are provided in U.S. Pat. Nos. 8,967,806 and 8,998,411.

Figure 11:
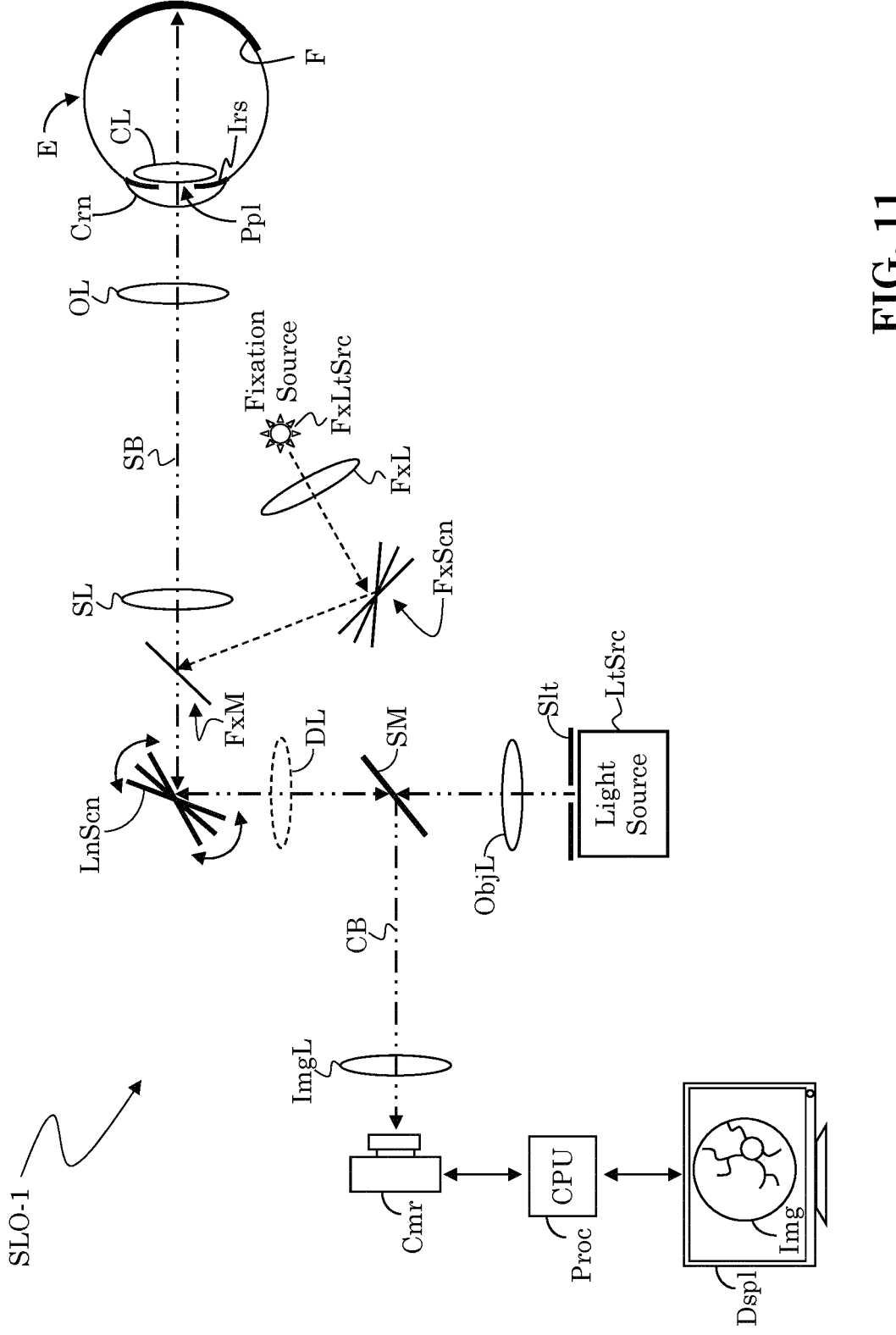
FIG. 11 illustrates an example of a slit scanning ophthalmic system for imaging a fundus.

FIG. 11 illustrates an example of a slit scanning ophthalmic system SLO-1 for imaging a fundus F, which is the interior surface of an eye E opposite the eye lens (or crystalline lens) CL and may include the retina, optic disc, macula, fovea, and posterior pole. In the present example, the imaging system is in a so-called "scan-descan" configuration, wherein a scanning line beam SB traverses the optical components of the eye E (including the cornea Crn, iris Irs, pupil Ppl, and crystalline lens CL) to be scanned across the fundus F. In the case of a flood fundus imager, no scanner is needed, and the light is applied across the entire, desired field of view (FOV) at once. Other scanning configurations are known in the art, and the specific scanning configuration is not critical to the present invention. As depicted, the imaging system includes one or more light sources LtSrc, preferably a multi-color LED system or a laser system in which the etendue has been suitably adjusted. An optional slit Slt (adjustable or static) is positioned in front of the light source LtSrc and may be used to adjust the width of the scanning line beam SB. Additionally, slit Slt may remain static during imaging or may be adjusted to different widths to allow for different confocality levels and different applications either for a particular scan or during the scan for use in suppressing reflexes. An optional objective lens ObjL may be placed in front of the slit Slt. The objective lens ObjL can be any one of state-of-the-art lenses including but not limited to refractive, diffractive, reflective, or hybrid lenses/ systems. The light from slit Slt passes through a pupil splitting mirror SM and is directed towards a scanner LnScn. It is desirable to bring the scanning plane and the pupil plane as near together as possible to reduce vignetting in the system. Optional optics DL may be included to manipulate the optical distance between the images of the two components. Pupil splitting mirror SM may pass an illumination beam from light source LtSrc to scanner LnScn, and reflect a detection beam from scanner LnScn (e.g., reflected light returning from eye E) toward a camera Cmr. A task of the pupil splitting mirror SM is to split the illumination and detection beams and to aid in the suppression of system reflexes. The scanner LnScn could be a rotating galvo scanner or other types of scanners (e.g., piezo or voice coil, micro-electromechanical system (MEMS) scanners, electro-optical deflectors, and/or rotating polygon scanners). Depending on whether the pupil splitting is done before or after the scanner LnScn, the scanning could be broken into two steps wherein one scanner is in an illumination path and a separate scanner is in a detection path. Specific pupil splitting arrangements are described in detail in U.S. Pat. No. 9,456,746, which is herein incorporated in its entirety by reference.

From the scanner LnScn, the illumination beam passes through one or more optics, in this case a scanning lens SL and an ophthalmic or ocular lens OL, that allow for the pupil of the eye E to be imaged to an image pupil of the system. Generally, the scan lens SL receives a scanning illumination beam from the scanner LnScn at any of multiple scan angles (incident angles), and produces scanning line beam SB with a substantially flat surface focal plane (e.g., a collimated light path). Ophthalmic lens OL may then focus the scanning line beam SB onto an object to be imaged. In the present example, ophthalmic lens OL focuses the scanning line beam SB onto the fundus F (or retina) of eye E to image the fundus. In this manner, scanning line beam SB creates a traversing scan line that travels across the fundus F. One possible configuration for these optics is a Kepler type telescope wherein the distance between the two lenses is selected to create an approximately telecentric intermediate fundus image (4-f configuration). The ophthalmic lens OL could be a single lens, an achromatic lens, or an arrangement of different lenses. All lenses could be refractive, diffractive, reflective or hybrid as known to one skilled in the art. The focal length(s) of the ophthalmic lens OL, scan lens SL and the size and/or form of the pupil splitting mirror SM and scanner LnScn could be different depending on the desired field of view (FOV), and so an arrangement in which multiple components can be switched in and out of the beam path, for example by using a flip in optic, a motorized wheel, or a detachable optical element, depending on the field of view can be envisioned. Since the field of view change results in a different beam size on the pupil, the pupil splitting can also be changed in conjunction with the change to the FOV. For example, a 45° to 60° field of view is a typical, or standard, FOV for fundus cameras. Higher fields of view, e.g., a widefield FOV, of 60°-120°, or more, may also be feasible. A widefield FOV may be desired for a combination of the Broad-Line Fundus Imager (BLFI) with another imaging modalities such as optical coherence tomography (OCT). The upper limit for the field of view may be determined by the accessible working distance in combination with the physiological conditions around the human eye. Because a typical human retina has a FOV of 140° horizontal and 80°-100° vertical, it may be desirable to have an asymmetrical field of view for the highest possible FOV on the system.

The scanning line beam SB passes through the pupil Ppl of the eye E and is directed towards the retinal, or fundus, surface F. The scanner LnScn1 adjusts the location of the light on the retina, or fundus, F such that a range of transverse locations on the eye E are illuminated. Reflected or scattered light (or emitted light in the case of fluorescence imaging) is directed back along as similar path as the illumination to define a collection beam CB on a detection path to camera Cmr.

In the "scan-descan" configuration of the present, exemplary slit scanning ophthalmic system SLO-1, light returning from the eye E is "descanned" by scanner LnScn on its way to pupil splitting mirror SM. That is, scanner LnScn scans the illumination beam from pupil splitting mirror SM to define the scanning illumination beam SB across eye E, but since scanner LnScn also receives returning light from eye E at the same scan position, scanner LnScn has the effect of descanning the returning light (e.g., cancelling the scanning action) to define a non-scanning (e.g., steady or stationary) collection beam from scanner LnScn to pupil splitting mirror SM, which folds the collection beam toward camera Cmr. At the pupil splitting mirror SM, the reflected light (or emitted light in the case of fluorescence imaging) is separated from the illumination light onto the detection path directed towards camera Cmr, which may be a digital camera having a photo sensor to capture an image. An imaging (e.g., objective) lens ImgL may be positioned in the detection path to image the fundus to the camera Cmr. As is the case for objective lens ObjL, imaging lens ImgL may be any type of lens known in the art (e.g., refractive, diffractive, reflective or hybrid lens). Additional operational details, in particular, ways to reduce artifacts in images, are described in PCT Publication No. WO2016/124644, the contents of which are herein incorporated in their entirety by reference. The camera Cmr captures the received image, e.g., it creates an image file, which can be further processed by one or more (electronic) processors or computing devices (e.g., the computer system of FIG. 20). Thus, the collection beam (returning from all scan positions of the scanning line beam SB) is collected by the camera Cmr, and a full-frame image Img may be constructed from a composite of the individually captured collection beams, such as by montaging. However, other scanning configuration are also contemplated, including ones where the illumination beam is scanned across the eye E and the collection beam is scanned across a photo sensor array of the camera. PCT Publication WO 2012/059236 and US Patent Publication No. 2015/0131050, herein incorporated by reference, describe several embodiments of slit scanning ophthalmoscopes including various designs where the returning light is swept across the camera's photo sensor array and where the returning light is not swept across the camera's photo sensor array.

In the present example, the camera Cmr is connected to a processor (e.g., processing module) Proc and a display (e.g., displaying module, computer screen, electronic screen, etc.) Dsp1, both of which can be part of the image system itself, or may be part of separate, dedicated processing and/or displaying unit(s), such as a computer system wherein data is passed from the camera Cmr to the computer system over a cable or computer network including wireless networks. The display and processor can be an all in one unit. The display can be a traditional electronic display/screen or of the touch screen type and can include a user interface for displaying information to and receiving information from an instrument operator, or user. The user can interact with the display using any type of user input device as known in the art including, but not limited to, mouse, knobs, buttons, pointer, and touch screen.

It may be desirable for a patient's gaze to remain fixed while imaging is carried out. One way to achieve this is to provide a fixation target that the patient can be directed to stare at. Fixation targets can be internal or external to the instrument depending on what area of the eye is to be imaged. One embodiment of an internal fixation target is shown in FIG. 11. In addition to the primary light source LtSrc used for imaging, a second optional light source FxLtSrc, such as one or more LEDs, can be positioned such that a light pattern is imaged to the retina using lens FxL, scanning element FxScn and reflector/mirror FxM. Fixation scanner FxScn can move the position of the light pattern and reflector FxM directs the light pattern from fixation scanner FxScn to the fundus F of eye E. Preferably, fixation scanner FxScn is position such that it is located at the pupil plane of the system so that the light pattern on the retina/fundus can be moved depending on the desired fixation location.

Slit-scanning ophthalmoscope systems are capable of operating in different imaging modes depending on the light source and wavelength selective filtering elements employed. True color reflectance imaging (imaging similar to that observed by the clinician when examining the eye using a hand-held or slit lamp ophthalmoscope) can be achieved when imaging the eye with a sequence of colored LEDs (red, blue, and green). Images of each color can be built up in steps with each LED turned on at each scanning position or each color image can be taken in its entirety separately. The three, color images can be combined to display the true color image, or they can be displayed individually to highlight different features of the retina. The red channel best highlights the choroid, the green channel highlights the retina, and the blue channel highlights the anterior retinal layers. Additionally, light at specific frequencies (e.g., individual colored LEDs or lasers) can be used to excite different fluorophores in the eye (e.g., autofluorescence) and the resulting fluorescence can be detected by filtering out the excitation wavelength.

The fundus imaging system can also provide an infrared reflectance image, such as by using an infrared laser (or other infrared light source). The infrared (IR) mode is advantageous in that the eye is not sensitive to the IR wavelengths. This may permit a user to continuously take images without disturbing the eye (e.g., in a preview/alignment mode) to aid the user during alignment of the instrument. Also, the IR wavelengths have increased penetration through tissue and may provide improved visualization of choroidal structures. In addition, fluorescein angiography (FA) and indocyanine green (ICG) angiography imaging can be accomplished by collecting images after a fluorescent dye has been injected into the subject's bloodstream. For example, in FA (and/or ICG) a series of time-lapse images may be captured after injecting a light-reactive dye (e.g., fluorescent dye) into a subject's bloodstream. It is noted that care must be taken since the fluorescent dye may lead to a life-threatening allergic reaction in a portion of the population. High contrast, greyscale images are captured using specific light frequencies selected to excite the dye. As the dye flows through the eye, various portions of the eye are made to glow brightly (e.g., fluoresce), making it possible to discern the progress of the dye, and hence the blood flow, through the eye.

Optical Coherence Tomography Imaging System

Generally, optical coherence tomography (OCT) uses low-coherence light to produce two-dimensional (2D) and three-dimensional (3D) internal views of biological tissue. OCT enables in vivo imaging of retinal structures. OCT angiography (OCTA) produces flow information, such as vascular flow from within the retina. Examples of OCT systems are provided in U.S. Pat. Nos. 6,741,359 and 9,706,915, and examples of an OCTA systems may be found in U.S. Pat. Nos. 9,700,206 and 9,759,544, all of which are herein incorporated in their entirety by reference. An exemplary OCT/OCTA system is provided herein.

Figure 12:
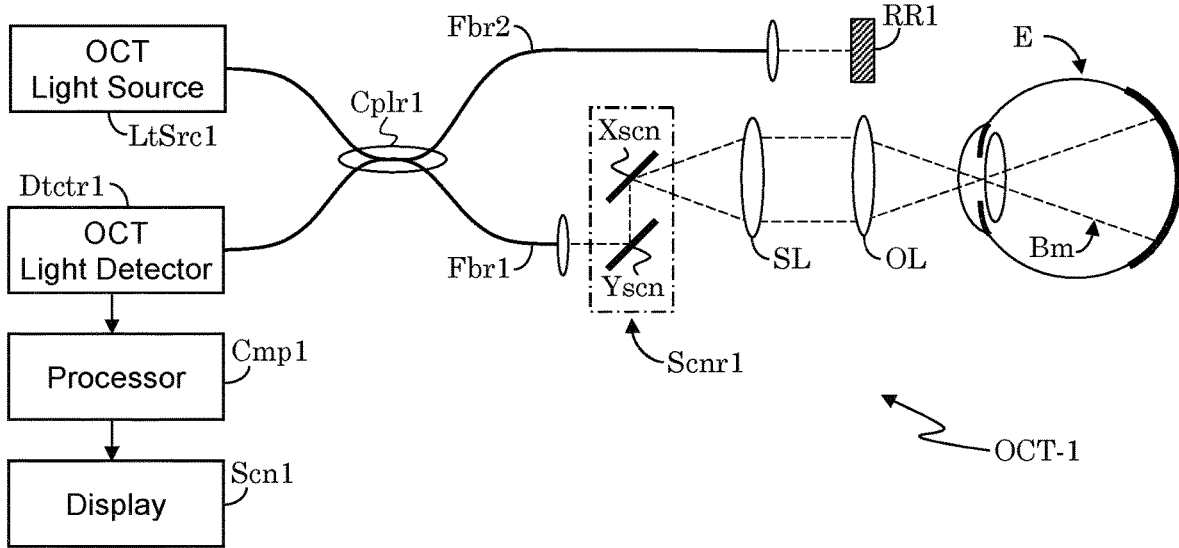
FIG. 12 illustrates a generalized frequency domain optical coherence tomography system used to collect 3D image data of the eye suitable for use with the present invention.

FIG. 12 illustrates a generalized frequency domain optical coherence tomography (FD-OCT) system used to collect 3D image data of the eye suitable for use with the present invention. An FD-OCT system OCT_1 includes a light source, LtSrc1. Typical light sources include, but are not limited to, broadband light sources with short temporal coherence lengths or swept laser sources. A beam of light from light source LtSrc1 is routed, typically by optical fiber Fbr1, to illuminate a sample, e.g., eye E; a typical sample being tissues in the human eye. The light source LrSrc1 may, for example, be a broadband light source with short temporal coherence length in the case of spectral domain OCT (SD-OCT) or a wavelength tunable laser source in the case of swept source OCT (SS-OCT). The light may be scanned, typically with a scanner Scnr1 between the output of the optical fiber Fbr1 and the sample E, so that the beam of light (dashed line Bm) is scanned laterally over the region of the sample to be imaged. The light beam from scanner Scnr1 may pass through a scan lens SL and an ophthalmic lens OL and be focused onto the sample E being imaged. The scan lens SL may receive the beam of light from the scanner Scnr1 at multiple incident angles and produces substantially collimated light, ophthalmic lens OL may then focus onto the sample. The present example illustrates a scan beam that needs to be scanned in two lateral directions (e.g., in x and y directions on a Cartesian plane) to scan a desired field of view (FOV). An example of this would be a point-field OCT, which uses a point-field beam to scan across a sample. Consequently, scanner Scnr1 is illustratively shown to include two sub-scanner: a first sub-scanner Xscn for scanning the point-field beam across the sample in a first direction (e.g., a horizontal x-direction); and a second sub-scanner Yscn for scanning the point-field beam on the sample in traversing second direction (e.g., a vertical y-direction). If the scan beam were a line-field beam (e.g., a line-field OCT), which may sample an entire line-portion of the sample at a time, then only one scanner may be needed to scan the line-field beam across the sample to span the desired FOV. If the scan beam were a full-field beam (e.g., a full-field OCT), no scanner may be needed, and the full-field light beam may be applied across the entire, desired FOV at once.

Figure 20:
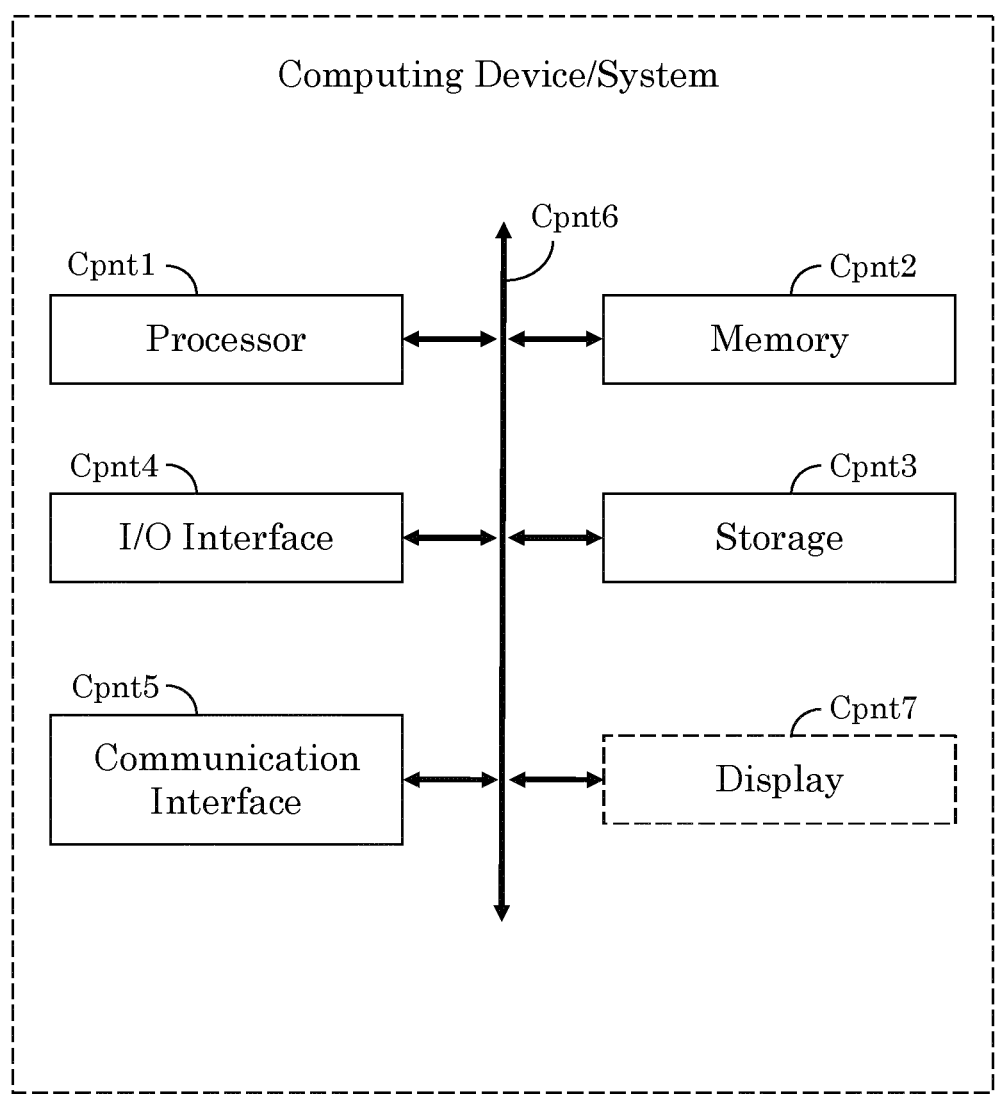
FIG. 20 illustrates an example computer system (or computing device or computer).

Irrespective of the type of beam used, light scattered from the sample (e.g., sample light) is collected. In the present example, scattered light returning from the sample is collected into the same optical fiber Fbr1 used to route the light for illumination. Reference light derived from the same light source LtSrc1 travels a separate path, in this case involving optical fiber Fbr2 and retro-reflector RR1 with an adjustable optical delay. Those skilled in the art will recognize that a transmissive reference path can also be used and that the adjustable delay could be placed in the sample or reference arm of the interferometer. Collected sample light is combined with reference light, for example, in a fiber coupler Cplr1, to form light interference in an OCT light detector Dtctr1 (e.g., photodetector array, digital camera, etc.). Although a single fiber port is shown going to the detector Dtctr1, those skilled in the art will recognize that various designs of interferometers can be used for balanced or unbalanced detection of the interference signal. The output from the detector Dtctr1 is supplied to a processor (e.g., internal or external computing device) Cmp1 that converts the observed interference into depth information of the sample. The depth information may be stored in a memory associated with the processor Cmp1 and/or displayed on a display (e.g., computer/electronic display/screen) Scn1. The processing and storing functions may be localized within the OCT instrument, or functions may be offloaded onto (e.g., performed on) an external processor (e.g., an external computing device), to which the collected data may be transferred. An example of a computing device (or computer system) is shown in FIG. 20. This unit could be dedicated to data processing or perform other tasks which are quite general and not dedicated to the OCT device. The processor (computing device) Cmp1 may include, for example, a field-programmable gate array (FPGA), a digital signal processor (DSP), an application specific integrated circuit (ASIC), a graphics processing unit (GPU), a system on chip (SoC), a central processing unit (CPU), a general purpose graphics processing unit (GPGPU), or a combination thereof, that may performs some, or the entire, processing steps in a serial and/or parallelized fashion with one or more host processors and/or one or more external computing devices.

The sample and reference arms in the interferometer could consist of bulk-optics, fiber-optics, or hybrid bulk-optic systems and could have different architectures such as Michelson, Mach-Zehnder or common-path based designs as would be known by those skilled in the art. Light beam as used herein should be interpreted as any carefully directed light path. Instead of mechanically scanning the beam, a field of light can illuminate a one or two-dimensional area of the retina to generate the OCT data (see for example, U.S. Pat. No. 9,332,902; D. Hillmann et al, "Holoscopy—Holographic Optical Coherence Tomography," *Optics Letters,* 36(13): 2390 2011; Y. Nakamura, et al, "High-Speed Three Dimensional Human Retinal Imaging by Line Field Spectral Domain Optical Coherence Tomography," *Optics Express,* 15(12):7103 2007; Blazkiewicz et al, "Signal-To-Noise Ratio Study of Full-Field Fourier-Domain Optical Coherence Tomography," *Applied Optics,* 44(36):7722 (2005)). In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system. Various aspects of the invention could apply to any type of OCT system or other types of ophthalmic diagnostic systems and/or multiple ophthalmic diagnostic systems including but not limited to fundus imaging systems, visual field test devices, and scanning laser polarimeters.

In Fourier Domain optical coherence tomography (FD-OCT), each measurement is the real-valued spectral interferogram (Sj(k)). The real-valued spectral data typically goes through several post-processing steps including background subtraction, dispersion correction, etc. The Fourier transform of the processed interferogram, results in a complex valued OCT signal output $Aj(z)=|Aj|e^{i\varphi}$. The absolute value of this complex OCT signal, $|Aj|$, reveals the profile of scattering intensities at different path lengths, and therefore scattering as a function of depth (z-direction) in the sample. Similarly, the phase, $\varphi j$ can also be extracted from the complex valued OCT signal. The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube. For a particular volume of data, the term fast axis refers to the scan direction along a single B-scan whereas slow axis refers to the axis along which multiple B-scans are collected. The term "cluster scan" may refer to a single unit or block of data generated by repeated acquisitions at the same (or substantially the same) location (or region) for the purposes of analyzing motion contrast, which may be used to identify blood flow. A cluster scan can consist of multiple A-scans or B-scans collected with relatively short time separations at approximately the same location(s) on the sample. Since the scans in a cluster scan are of the same region, static structures remain relatively unchanged from scan to scan within the cluster scan, whereas motion contrast between the scans that meets predefined criteria may be identified as blood flow.

A variety of ways to create B-scans are known in the art including but not limited to: along the horizontal or x-direction, along the vertical or y-direction, along the diagonal of x and y, or in a circular or spiral pattern. B-scans may be in the x-z dimensions but may be any cross-sectional image that includes the z-dimension. An example OCT B-scan image of a normal retina of a human eye is illustrated in FIG. 13. An OCT B-scan of the retinal provides a view of the structure of retinal tissue. For illustration purposes, FIG. 13 identifies various canonical retinal layers and layer boundaries. The identified retinal boundary layers include (from top to bottom): the inner limiting membrane (ILM) Lyer1, the retinal nerve fiber layer (BNFL or NFL) Layr2, the ganglion cell layer (GCL) Layr3, the inner plexiform layer (IPL) Layr4, the inner nuclear layer (INL) Layr5, the outer plexiform layer (OPL) Layr6, the outer nuclear layer (ONL) Layr7, the junction between the outer segments (OS) and inner segments (IS) (indicated by reference character Layr8) of the photoreceptors, the external or outer limiting membrane (ELM or OLM) Layr9, the retinal pigment epithelium (RPE) Layr10, and the Bruch's membrane (BM) Layr11.

In OCT Angiography, or Functional OCT, analysis algorithms may be applied to OCT data collected at the same, or approximately the same, sample locations on a sample at different times (e.g., a cluster scan) to analyze motion or flow (see for example US Patent Publication Nos. 2005/0171438, 2012/0307014, 2010/0027857, 2012/0277579 and U.S. Pat. No. No. 6,549,801, all of which are herein incorporated in their entirety by reference). An OCT system may use any one of a number of OCT angiography processing algorithms (e.g., motion contrast algorithms) to identify blood flow. For example, motion contrast algorithms can be applied to the intensity information derived from the image data (intensity-based algorithm), the phase information from the image data (phase-based algorithm), or the complex image data (complex-based algorithm). An en face image is a 2D projection of 3D OCT data (e.g., by averaging the intensity of each individual A-scan, such that each A-scan defines a pixel in the 2D projection). Similarly, an en face vasculature image is an image displaying motion contrast signal in which the data dimension corresponding to depth (e.g., z-direction along an A-scan) is displayed as a single representative value (e.g., a pixel in a 2D projection image), typically by summing or integrating all or an isolated portion of the data (see for example U.S. Pat. No. 7,301,644 herein incorporated in its entirety by reference). OCT systems that provide an angiography imaging functionality may be termed OCT angiography (OCTA) systems.

Figure 14:
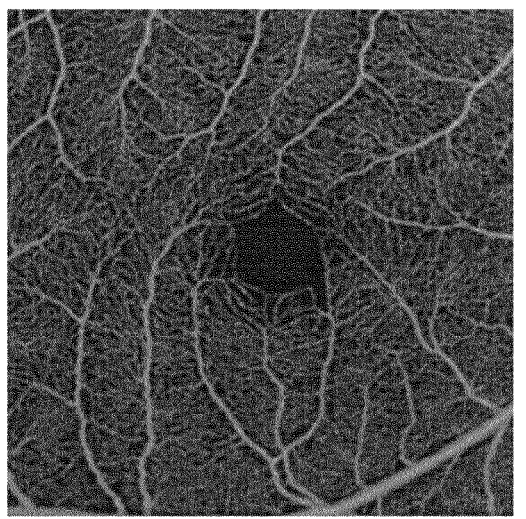
FIG. 14 shows an example of an en face vasculature image.
Figure 15:
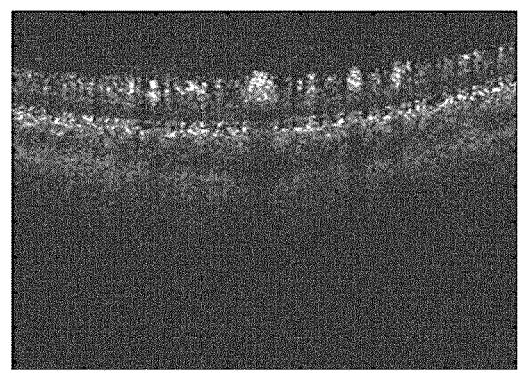
FIG. 15 shows an exemplary B-scan of a vasculature (OCTA) image.

FIG. 14 shows an example of an en face vasculature image. After processing the data to highlight motion contrast using any of the motion contrast techniques known in the art, a range of pixels corresponding to a given tissue depth from the surface of internal limiting membrane (ILM) in retina, may be summed to generate the en face (e.g., frontal view) image of the vasculature. FIG. 15 shows an exemplary B-scan of a vasculature (OCTA) image. As illustrated, structural information may not be well-defined since blood flow may traverse multiple retinal layers making them less defined than in a structural OCT B-scan, as shown in FIG. 13. Nonetheless, OCTA provides a non-invasive technique for imaging the microvasculature of the retina and the choroid, which may be critical to diagnosing and/or monitoring various pathologies. For example, OCTA may be used to identify diabetic retinopathy by identifying microaneurysms, neovascular complexes, and quantifying foveal avascular zone and nonperfused areas. Moreover, OCTA has been shown to be in good agreement with fluorescein angiography (FA), a more traditional, but more evasive, technique requiring the injection of a dye to observe vascular flow in the retina. Additionally, in dry age-related macular degeneration, OCTA has been used to monitor a general decrease in choriocapillaris flow. Similarly in wet age-related macular degeneration, OCTA can provides a qualitative and quantitative analysis of choroidal neovascular membranes. OCTA has also been used to study vascular occlusions, e.g., evaluation of nonperfused areas and the integrity of superficial and deep plexus.

Neural Networks

As discussed above, the present invention may use a neural network (NN) machine learning (ML) model. For the sake of completeness, a general discussion of neural networks is provided herein. The present invention may use any, singularly or in combination, of the below described neural network architecture(s). A neural network, or neural net, is a (nodal) network of interconnected neurons, where each neuron represents a node in the network. Groups of neurons may be arranged in layers, with the outputs of one layer feeding forward to a next layer in a multilayer perceptron (MLP) arrangement. MLP may be understood to be a feedforward neural network model that maps a set of input data onto a set of output data.

Figure 16:
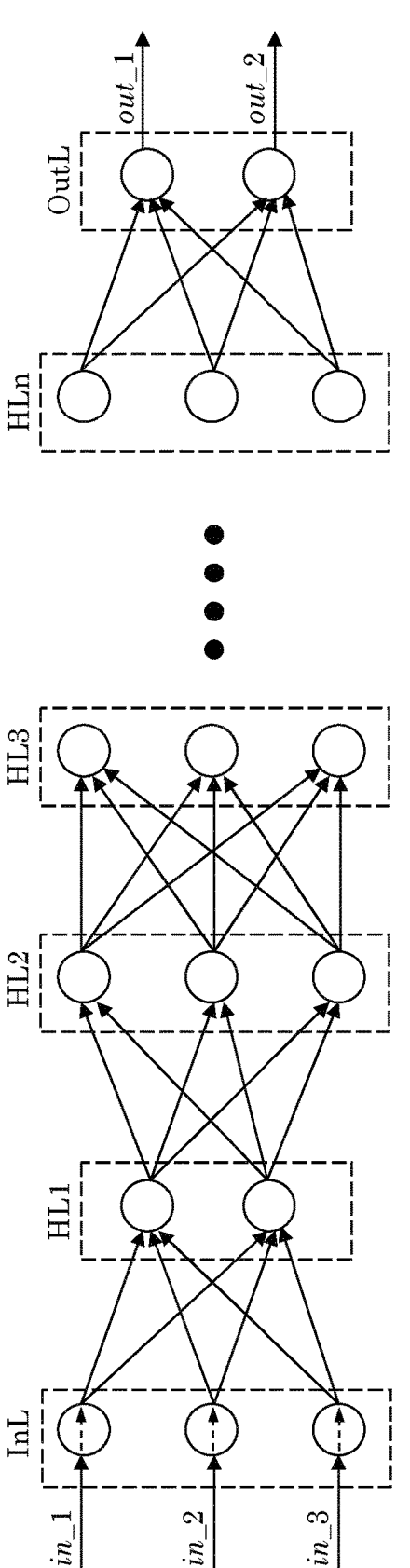
FIG. 16 illustrates an example of a multilayer perceptron (MLP) neural network.

FIG. 16 illustrates an example of a multilayer perceptron (MLP) neural network. Its structure may include multiple hidden (e.g., internal) layers HL1 to HLn that map an input layer InL (that receives a set of inputs (or vector input) in_1 to in_3) to an output layer OutL that produces a set of outputs (or vector output), e.g., out_1 and out_2. Each layer may have any given number of nodes, which are herein illustratively shown as circles within each layer. In the present example, the first hidden layer HL1 has two nodes, while hidden layers HL2, HL3, and HLn each have three nodes. Generally, the deeper the MLP (e.g., the greater the number of hidden layers in the MLP), the greater its capacity to learn. The input layer InL receives a vector input (illustratively shown as a three-dimensional vector consisting of in_1, in_2 and in_3), and may apply the received vector input to the first hidden layer HL1 in the sequence of hidden layers. An output layer OutL receives the output from the last hidden layer, e.g., HLn, in the multilayer model, processes its inputs, and produces a vector output result (illustratively shown as a two-dimensional vector consisting of out_1 and out_2).

Typically, each neuron (or node) produces a single output that is fed forward to neurons in the layer immediately following it. But each neuron in a hidden layer may receive multiple inputs, either from the input layer or from the outputs of neurons in an immediately preceding hidden layer. In general, each node may apply a function to its inputs to produce an output for that node. Nodes in hidden layers (e.g., learning layers) may apply the same function to their respective input(s) to produce their respective output (s). Some nodes, however, such as the nodes in the input layer InL receive only one input and may be passive, meaning that they simply relay the values of their single input to their output(s), e.g., they provide a copy of their input to their output(s), as illustratively shown by dotted arrows within the nodes of input layer InL.

Figure 17:
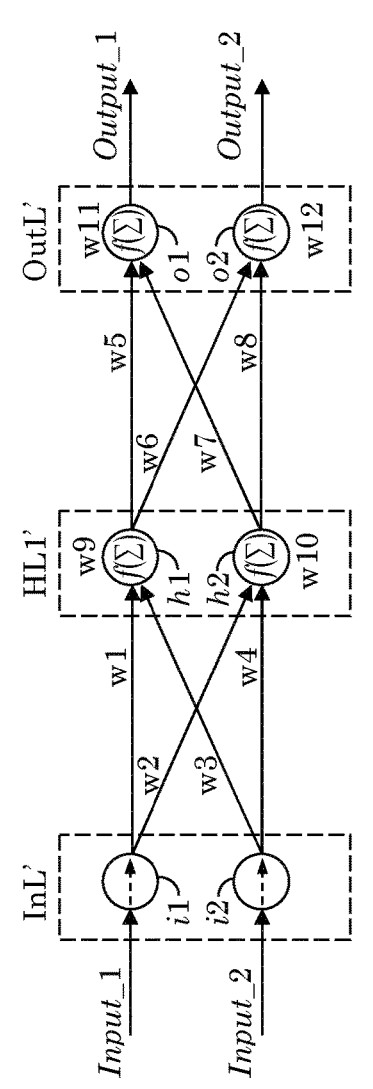
FIG. 17 shows a simplified neural network consisting of an input layer, a hidden layer, and an output layer.

For illustration purposes, FIG. 17 shows a simplified neural network consisting of an input layer InL', a hidden layer HL1', and an output layer OutL'. Input layer InL' is shown having two input nodes i1 and i2 that respectively receive inputs Input_1 and Input_2 (e.g. the input nodes of layer InL' receive an input vector of two dimensions). The input layer InL' feeds forward to one hidden layer HL1' having two nodes h1 and h2, which in turn feeds forward to an output layer OutL' of two nodes o1 and o2. Interconnections, or links, between neurons (illustrative shown as solid arrows) have weights w1 to w8. Typically, except for the input layer, a node (neuron) may receive as input the outputs of nodes in its immediately preceding layer. Each node may calculate its output by multiplying each of its inputs by each input's corresponding interconnection weight, summing the products of it inputs, adding (or multiplying by) a constant defined by another weight or bias that may be associated with that particular node (e.g., node weights w9, w10, w11, w12 respectively corresponding to nodes h1, h2, o1, and o2), and then applying a non-linear function or logarithmic function to the result. The non-linear function may be termed an activation function or transfer function. Multiple activation functions are known the art, and selection of a specific activation function is not critical to the present discussion. It is noted, however, that operation of the ML model, or behavior of the neural net, is dependent upon weight values, which may be learned so that the neural network provides a desired output for a given input.

The neural net learns (e.g., is trained to determine) appropriate weight values to achieve a desired output for a given input during a training, or learning, stage. Before the neural net is trained, each weight may be individually assigned an initial (e.g., random and optionally non-zero) value, e.g. a random-number seed. Various methods of assigning initial weights are known in the art. The weights are then trained (optimized) so that for a given training vector input, the neural network produces an output close to a desired (predetermined) training vector output. For example, the weights may be incrementally adjusted in thousands of iterative cycles by a technique termed back-propagation. In each cycle of back-propagation, a training input (e.g., vector input or training input image/sample) is fed forward through the neural network to determine its actual output (e.g., vector output). An error for each output neuron, or output node, is then calculated based on the actual neuron output and a target training output for that neuron (e.g., a training output image/sample corresponding to the present training input image/sample). One then propagates back through the neural network (in a direction from the output layer back to the input layer) updating the weights based on how much effect each weight has on the overall error so that the output of the neural network moves closer to the desired training output. This cycle is then repeated until the actual output of the neural network is within an acceptable error range of the desired training output for the given training input. As it would be understood, each training input may require many back-propagation iterations before achieving a desired error range. Typically, an epoch refers to one back-propagation iteration (e.g., one forward pass and one backward pass) of all the training samples, such that training a neural network may require many epochs. Generally, the larger the training set, the better the performance of the trained ML model, so various data augmentation methods may be used to increase the size of the training set. For example, when the training set includes pairs of corresponding training input images and training output images, the training images may be divided into multiple corresponding image segments (or patches). Corresponding patches from a training input image and training output image may be paired to define multiple training patch pairs from one input/output image pair, which enlarges the training set. Training on large training sets, however, places high demands on computing resources, e.g. memory and data processing resources. Computing demands may be reduced by dividing a large training set into multiple mini-batches, where the mini-batch size defines the number of training samples in one forward/backward pass. In this case, and one epoch may include multiple mini-batches. Another issue is the possibility of a NN overfitting a training set such that its capacity to generalize from a specific input to a different input is reduced. Issues of overfitting may be mitigated by creating an ensemble of neural networks or by randomly dropping out nodes within a neural network during training, which effectively removes the dropped nodes from the neural network. Various dropout regulation methods, such as inverse dropout, are known in the art.

It is noted that the operation of a trained NN machine model is not a straight-forward algorithm of operational/ analyzing steps. Indeed, when a trained NN machine model receives an input, the input is not analyzed in the traditional sense. Rather, irrespective of the subject or nature of the input (e.g., a vector defining a live image/scan or a vector defining some other entity, such as a demographic description or a record of activity) the input will be subjected to the same predefined architectural construct of the trained neural network (e.g., the same nodal/layer arrangement, trained weight and bias values, predefined convolution/deconvolution operations, activation functions, pooling operations, etc.), and it may not be clear how the trained network's architectural construct produces its output. Furthermore, the values of the trained weights and biases are not deterministic and depend upon many factors, such as the amount of time the neural network is given for training (e.g., the number of epochs in training), the random starting values of the weights before training starts, the computer architecture of the machine on which the NN is trained, selection of training samples, distribution of the training samples among multiple mini-batches, choice of activation function(s), choice of error function(s) that modify the weights, and even if training is interrupted on one machine (e.g., having a first computer architecture) and completed on another machine (e.g., having a different computer architecture). The point is that the reasons why a trained ML model reaches certain outputs is not clear, and much research is currently ongoing to attempt to determine the factors on which a ML model bases its outputs. Therefore, the processing of a neural network on live data cannot be reduced to a simple algorithm of steps. Rather, its operation is dependent upon its training architecture, training sample sets, training sequence, and various circumstances in the training of the ML model.

In summary, construction of a NN machine learning model may include a learning (or training) stage and a classification (or operational) stage. In the learning stage, the neural network may be trained for a specific purpose and may be provided with a set of training examples, including training (sample) inputs and training (sample) outputs, and optionally including a set of validation examples to test the progress of the training. During this learning process, various weights associated with nodes and node-interconnections in the neural network are incrementally adjusted in order to reduce an error between an actual output of the neural network and the desired training output. In this manner, a multi-layer feed-forward neural network (such as discussed above) may be made capable of approximating any measurable function to any desired degree of accuracy. The result of the learning stage is a (neural network) machine learning (ML) model that has been learned (e.g., trained). In the operational stage, a set of test inputs (or live inputs) may be submitted to the learned (trained) ML model, which may apply what it has learned to produce an output prediction based on the test inputs.

Like the regular neural networks of FIGS. 16 and 17, convolutional neural networks (CNN) are also made up of neurons that have learnable weights and biases. Each neuron receives inputs, performs an operation (e.g., dot product), and is optionally followed by a non-linearity. The CNN, however, may receive raw image pixels at one end (e.g., the input end) and provide classification (or class) scores at the other end (e.g., the output end). Because CNNs expect an image as input, they are optimized for working with volumes (e.g., pixel height and width of an image, plus the depth of the image, e.g., color depth such as an RGB depth defined of three colors: red, green, and blue). For example, the layers of a CNN may be optimized for neurons arranged in 3 dimensions. The neurons in a CNN layer may also be connected to a small region of the layer before it, instead of all of the neurons in a fully-connected NN. The final output layer of a CNN may reduce a full image into a single vector (classification) arranged along the depth dimension.

Figure 18:
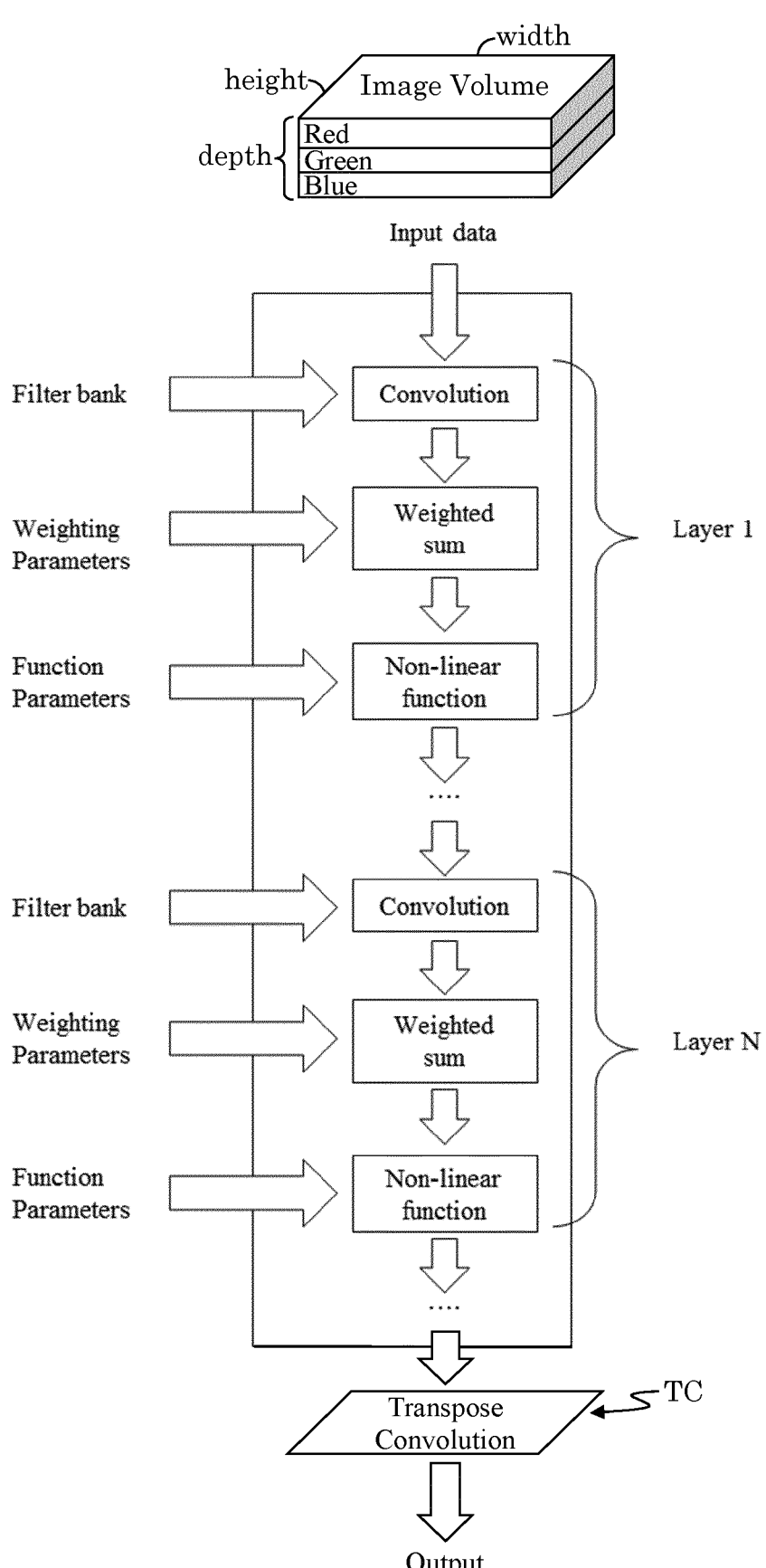
FIG. 18 illustrates an example convolutional neural network architecture.

FIG. 18 provides an example convolutional neural network architecture. A convolutional neural network may be defined as a sequence of two or more layers (e.g., Layer 1 to Layer N), where a layer may include a (image) convolution step, a weighted sum (of results) step, and a non-linear function step. The convolution may be performed on its input data by applying a filter (or kernel), e.g. on a moving window across the input data, to produce a feature map. Each layer and component of a layer may have different pre-determined filters (from a filter bank), weights (or weighting parameters), and/or function parameters. In the present example, the input data is an image, which may be raw pixel values of the image, of a given pixel height and width. In the present example, the input image is illustrated as having a depth of three color channels RGB (Red, Green, and Blue). Optionally, the input image may undergo various preprocessing, and the preprocessing results may be input in place of, or in addition to, the raw input image. Some examples of image preprocessing may include: retina blood vessel map segmentation, color space conversion, adaptive histogram equalization, connected components generation, etc. Within a layer, a dot product may be computed between the given weights and a small region they are connected to in the input volume. Many ways of configuring a CNN are known in the art, but as an example, a layer may be configured to apply an elementwise activation function, such as max (0,x) thresholding at zero. A pooling function may be performed (e.g., along the x-y directions) to down-sample a volume. A fully-connected layer may be used to determine the classification output and produce a one-dimensional output vector, which has been found useful for image recognition and classification. However, for image segmentation, the CNN would need to classify each pixel. Since each CNN layers tends to reduce the resolution of the input image, another stage is needed to up-sample the image back to its original resolution. This may be achieved by application of a transpose convolution (or deconvolution) stage TC, which typically does not use any predefine interpolation method, and instead has learnable parameters.

Convolutional Neural Networks have been successfully applied to many computer vision problems. As explained above, training a CNN generally requires a large training dataset. The U-Net architecture is based on CNNs and can generally be trained on a smaller training dataset than conventional CNNs.

Figure 19:
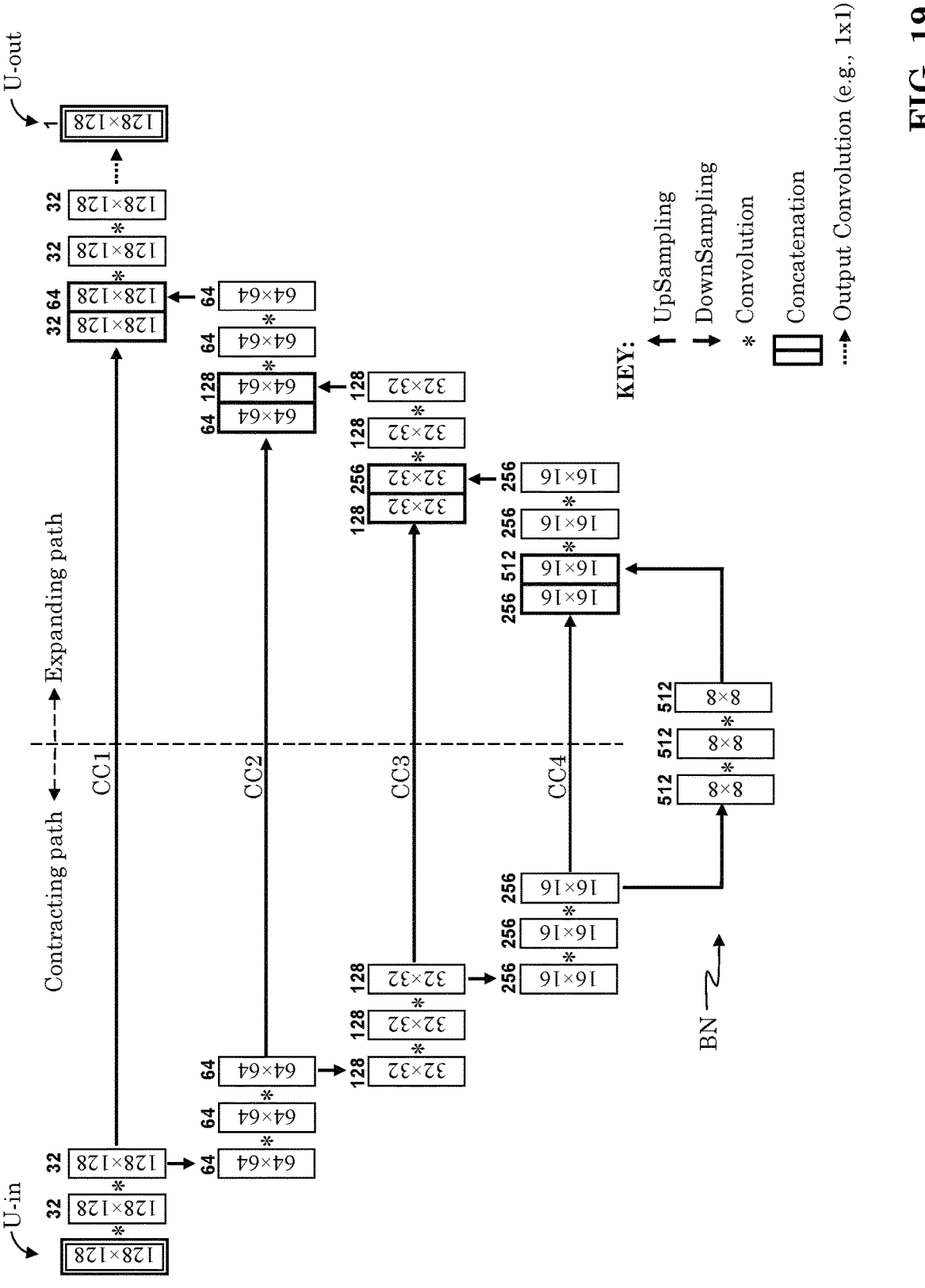
FIG. 19 illustrates an example U-Net architecture.

FIG. 19 illustrates an example U-Net architecture. The present exemplary U-Net includes an input module (or input layer or stage) that receives an input U-in (e.g., input image or image patch) of any given size. For illustration purposes, the image size at any stage, or layer, is indicated within a box that represents the image, e.g., the input module encloses number "128×128" to indicate that input image U-in is comprised of 128 by 128 pixels. The input image may be a fundus image, an OCT/OCTA en face, B-scan image, etc. It is to be understood, however, that the input may be of any size or dimension. For example, the input image may be a multi-channel image (e.g., an RGB color image), monochrome image, volume image, etc. The input image undergoes a series of processing layers, each of which is illustrated with exemplary sizes, but these sizes are illustration purposes only and would depend, for example, upon the size of the image, convolution filter, and/or pooling stages. The present architecture consists of a contracting path (herein illustratively comprised of four encoding modules) followed by an expanding path (herein illustratively comprised of four decoding modules), and copy-and-crop links (e.g., CC1 to CC4) between corresponding modules/stages that copy the output of one encoding module in the contracting path and concatenates it to (e.g., appends it to the back of) the up-converted input of a correspond decoding module in the expanding path. This results in a characteristic U-shape, from which the architecture draws its name. Optionally, such as for computational considerations, a "bottleneck" module/stage (BN) may be positioned between the contracting path and the expanding path. The bottleneck BN may consist of two convolutional layers (with batch normalization and optional dropout).

The contracting path is similar to an encoder, and generally captures context (or feature) information by the use of feature maps. In the present example, each encoding module in the contracting path may include two or more convolutional layers, illustratively indicated by an asterisk symbol "*", and which may be followed by a max pooling layer (e.g., DownSampling layer). For example, input image U-in is illustratively shown to undergo two convolution layers, each with 32 feature maps. As it would be understood, each convolution kernel produces a feature map (e.g., the output from a convolution operation with a given kernel is an image typically termed a "feature map"). For example, input U-in undergoes a first convolution that applies 32 convolution kernels (not shown) to produce an output consisting of 32 respective feature maps. However, as it is known in the art, the number of feature maps produced by a convolution operation may be adjusted (up or down). For example, the number of feature maps may be reduced by averaging groups of feature maps, dropping some feature maps, or other known method of feature map reduction. In the present example, this first convolution is followed by a second convolution whose output is limited to 32 feature maps. Another way to envision feature maps may be to think of the output of a convolution layer as a 3D image whose 2D dimension is given by the listed X-Y planar pixel dimension (e.g., 128×128 pixels), and whose depth is given by the number of feature maps (e.g., 32 planar images deep). Following this analogy, the output of the second convolution (e.g., the output of the first encoding module in the contracting path) may be described as a 128×128×32 image. The output from the second convolution then undergoes a pooling operation, which reduces the 2D dimension of each feature map (e.g., the X and Y dimensions may each be reduced by half). The pooling operation may be embodied within the DownSampling operation, as indicated by a downward arrow. Several pooling methods, such as max pooling, are known in the art and the specific pooling method is not critical to the present invention. The number of feature maps may double at each pooling, starting with 32 feature maps in the first encoding module (or block), 64 in the second encoding module, and so on. The contracting path thus forms a convolutional network consisting of multiple encoding modules (or stages or blocks). As is typical of convolutional networks, each encoding module may provide at least one convolution stage followed by an activation function (e.g., a rectified linear unit (ReLU) or sigmoid layer), not shown, and a max pooling operation. Generally, an activation function introduces non-linearity into a layer (e.g., to help avoid overfitting issues), receives the results of a layer, and determines whether to "activate" the output (e.g., determines whether the value of a given node meets predefined criteria to have an output forwarded to a next layer/node). In summary, the contracting path generally reduces spatial information while increasing feature information.

The expanding path is similar to a decoder, and among other things, may provide localization and spatial information for the results of the contracting path, despite the down sampling and any max-pooling performed in the contracting stage. The expanding path includes multiple decoding modules, where each decoding module concatenates its current up-converted input with the output of a corresponding encoding module. In this manner, feature and spatial information are combined in the expanding path through a sequence of up-convolutions (e.g., UpSampling or transpose convolutions or deconvolutions) and concatenations with high-resolution features from the contracting path (e.g., via CC1 to CC4). Thus, the output of a deconvolution layer is concatenated with the corresponding (optionally cropped) feature map from the contracting path, followed by two convolutional layers and activation function (with optional batch normalization).

The output from the last expanding module in the expanding path may be fed to another processing/training block or layer, such as a classifier block, that may be trained along with the U-Net architecture. Alternatively, or in addition, the output of the last upsampling block (at the end of the expanding path) may be submitted to another convolution (e.g., an output convolution) operation, as indicated by a dotted arrow, before producing its output U-out. The kernel size of output convolution may be selected to reduce the dimensions of the last upsampling block to a desired size. For example, the neural network may have multiple features per pixels right before reaching the output convolution, which may provide a 1×1 convolution operation to combine these multiple features into a single output value per pixel, on a pixel-by-pixel level.

Computing Device/System

FIG. 20 illustrates an example computer system (or computing device or computer device). In some embodiments, one or more computer systems may provide the functionality described or illustrated herein and/or perform one or more steps of one or more methods described or illustrated herein. The computer system may take any suitable physical form. For example, the computer system may be an embedded computer system, a system-on-chip (SOC), a single-board computer system (SBC) (such as, for example, a computer-on-module (COM) or system-on-module (SOM)), a desktop computer system, a laptop or notebook computer system, a mesh of computer systems, a mobile telephone, a personal digital assistant (PDA), a server, a tablet computer system, an augmented/virtual reality device, or a combination of two or more of these. Where appropriate, the computer system may reside in a cloud, which may include one or more cloud components in one or more networks.

In some embodiments, the computer system may include a processor Cpnt1, memory Cpnt2, storage Cpnt3, an input/ output (I/O) interface Cpnt4, a communication interface Cpnt5, and a bus Cpnt6. The computer system may optionally also include a display Cpnt7, such as a computer monitor or screen.

Processor Cpnt1 includes hardware for executing instructions, such as those making up a computer program. For example, processor Cpnt1 may be a central processing unit (CPU) or a general-purpose computing on graphics processing unit (GPGPU). Processor Cpnt1 may retrieve (or fetch) the instructions from an internal register, an internal cache, memory Cpnt2, or storage Cpnt3, decode and execute the instructions, and write one or more results to an internal register, an internal cache, memory Cpnt2, or storage Cpnt3. In particular embodiments, processor Cpnt1 may include one or more internal caches for data, instructions, or addresses. Processor Cpnt1 may include one or more instruction caches, one or more data caches, such as to hold data tables. Instructions in the instruction caches may be copies of instructions in memory Cpnt2 or storage Cpnt3, and the instruction caches may speed up retrieval of those instructions by processor Cpnt1. Processor Cpnt1 may include any suitable number of internal registers, and may include one or more arithmetic logic units (ALUs). Processor Cpnt1 may be a multi-core processor; or include one or more processors Cpnt1. Although this disclosure describes and illustrates a particular processor, this disclosure contemplates any suitable processor.

Memory Cpnt2 may include main memory for storing instructions for processor Cpnt1 to execute or to hold interim data during processing. For example, the computer system may load instructions or data (e.g., data tables) from storage Cpnt3 or from another source (such as another computer system) to memory Cpnt2. Processor Cpnt1 may load the instructions and data from memory Cpnt2 to one or more internal register or internal cache. To execute the instructions, processor Cpnt1 may retrieve and decode the instructions from the internal register or internal cache. During or after execution of the instructions, processor Cpnt1 may write one or more results (which may be intermediate or final results) to the internal register, internal cache, memory Cpnt2 or storage Cpnt3. Bus Cpnt6 may include one or more memory buses (which may each include an address bus and a data bus) and may couple processor Cpnt1 to memory Cpnt2 and/or storage Cpnt3. Optionally, one or more memory management unit (MMU) facilitate data transfers between processor Cpnt1 and memory Cpnt2. Memory Cpnt2 (which may be fast, volatile memory) may include random access memory (RAM), such as dynamic RAM (DRAM) or static RAM (SRAM). Storage Cpnt3 may include long-term or mass storage for data or instructions. Storage Cpnt3 may be internal or external to the computer system, and include one or more of a disk drive (e.g., hard-disk drive, HDD, or solid-state drive, SSD), flash memory, ROM, EPROM, optical disc, magneto-optical disc, magnetic tape, Universal Serial Bus (USB)-accessible drive, or other type of non-volatile memory.

I/O interface Cpnt4 may be software, hardware, or a combination of both, and include one or more interfaces (e.g., serial or parallel communication ports) for communication with I/O devices, which may enable communication with a person (e.g., user). For example, I/O devices may include a keyboard, keypad, microphone, monitor, mouse, printer, scanner, speaker, still camera, stylus, tablet, touch screen, trackball, video camera, another suitable I/O device, or a combination of two or more of these.

Communication interface Cpnt5 may provide network interfaces for communication with other systems or networks. Communication interface Cpnt5 may include a Bluetooth interface or other type of packet-based communication. For example, communication interface Cpnt5 may include a network interface controller (NIC) and/or a wireless NIC or a wireless adapter for communicating with a wireless network. Communication interface Cpnt5 may provide communication with a WI-FI network, an ad hoc network, a personal area network (PAN), a wireless PAN (e.g., a Bluetooth WPAN), a local area network (LAN), a wide area network (WAN), a metropolitan area network (MAN), a cellular telephone network (such as, for example, a Global System for Mobile Communications (GSM) network), the Internet, or a combination of two or more of these.

Bus Cpnt6 may provide a communication link between the above-mentioned components of the computing system. For example, bus Cpnt6 may include an Accelerated Graphics Port (AGP) or other graphics bus, an Enhanced Industry Standard Architecture (EISA) bus, a front-side bus (FSB), a HyperTransport (HT) interconnect, an Industry Standard Architecture (ISA) bus, an InfiniBand bus, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or other suitable bus or a combination of two or more of these.

Although this disclosure describes and illustrates a particular computer system having a particular number of particular components in a particular arrangement, this disclosure contemplates any suitable computer system having any suitable number of any suitable components in any suitable arrangement.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

While the invention has been described in conjunction with several specific embodiments, it is evident to those skilled in the art that many further alternatives, modifications, and variations will be apparent in light of the foregoing description. Thus, the invention described herein is intended to embrace all such alternatives, modifications, applications and variations as may fall within the spirit and scope of the appended claims.

The invention claimed is:

1. A method of analyzing optical coherence tomography (OCT) data, comprising:

collecting the OCT data with an OCT system, the OCT data including a plurality of A-scans;

using an electronic data processor:

extracting a series of metrics from each individual A-scan;

defining a set of images based on the extracted metrics, each image defining pathology-characteristic data;

defining a multi-channel image based on the set of images;

submitting the multi-channel image into a machine learning model trained to identify one or more pathologies based on the pathology-characteristic data; and displaying or storing for future processing the identified pathology, wherein the pathology is geographic atrophy, wherein the series of metrics include two or more of sub-RPE (retinal pigment epithelium) reflectivity, inner RPE reflectivity, retinal thickness, choriocapillaris flow, and optical attenuation coefficient (OAC); and wherein each metric defines a separate corresponding channel per pixel of the multi-channel image.

2. The method of claim 1, wherein the collected OCT data is volume data and each image in the set of images is a two-dimensional image.

3. The method of claim 1, wherein a pixel channel within the multiple channel image specifies a relative distance from a pixel's corresponding A-scan to a predefined ophthalmic landmark.

4. The method of claim 3, wherein the pixels are based on distances from each A-scan to the fovea.

5. The method of claim 1, further including accessing additional imaging data of one or more additional imaging modalities different than OCT, wherein the multi-channel image includes one or more image channels respectively based on the one or more additional imaging modalities.

6. The method of claim 5, wherein the one or more additional images are based on at least one of a fundus image, autofluorescence image, fluorescein angiography image, OCT angiography image, or visual field test map.

7. The method of claim 5, wherein the machine learning model is further trained using non-image data.

8. The method of claim 7, wherein the non-image data includes patient demographic data.

9. The method of claim 1, further including:

acquiring visual field functional data, the multi-channel image including at least one image channel based on the visual field functional data.

10. The method of claim 1, further including:

sorting the extracted metrics from each A-scan into corresponding metric groups with a one-to-one correspondence.

11. The method of claim 10, wherein each channel of the multi-channel image is based on a corresponding metric group.

12. The method of claim 1, wherein the extracted metrics from each A-scan are associated with the same pathology type.

13. The method of claim 1, wherein:

the OCT data includes OCT structural data and OCT angiography (OCTA) flow data; the series of metrics include OCT-based metrics extracted from the OCT structural data and OCTA-based metrics extracted from the OCTA flow data;

the set of images includes OCT-based images based on the OCT-based metrics and OCTA-based images based on OCTA-based metrics; and the multi-channel image is based on the OCT-based images and OCTA-based images.

14. The method of claim 1, wherein the machine learning model identifies a region of the multi-channel image where the pathology is present based on a combination of pathology-characteristic data provided by the individual channels of each pixel of the multi-channel image.

15. The method of claim 14, wherein each A-scan is mapped to a pixel in the multi-channel image, and the identified region where the pathology is present is mapped to the collected OCT data.

16. The method of claim 1, wherein the machine learning model is embodied by a neural network.

17. The method of claim 16, wherein the neural network is a U-Net type architecture.

18. The method of claim 1, wherein each channel in the multi-channel image is a color channel.

* * * * *